(12) United States Patent
Cotner

(10) Patent No.: US 9,808,329 B2
(45) Date of Patent: Nov. 7, 2017

(54) DEVICE FOR PREVENTING OVEREXPANSION OF BODILY ORGAN

(71) Applicant: Ronald L. Cotner, Lakeland, FL (US)

(72) Inventor: Ronald L. Cotner, Lakeland, FL (US)

( * ) Notice: Subject to any disclaimer, the term of this patent is extended or adjusted under 35 U.S.C. 154(b) by 280 days.

(21) Appl. No.: 14/594,455

(22) Filed: Jan. 12, 2015

(65) Prior Publication Data

US 2016/0199167 A1 Jul. 14, 2016

(51) Int. Cl.
*A61F 2/00* (2006.01)
*A61B 17/12* (2006.01)
*A61F 5/00* (2006.01)
*A61B 17/00* (2006.01)

(52) U.S. Cl.
CPC ...... *A61F 2/0036* (2013.01); *A61B 17/12013* (2013.01); *A61F 2/004* (2013.01); *A61F 5/005* (2013.01); *A61B 2017/00557* (2013.01); *A61B 2017/00827* (2013.01); *A61B 2017/00893* (2013.01); *A61F 2210/0057* (2013.01)

(58) Field of Classification Search
CPC ........ A61F 2/0036; A61F 5/005; A61F 2/004; A61F 2210/0057; A61B 17/12013; A61B 17/12
See application file for complete search history.

(56) References Cited

U.S. PATENT DOCUMENTS

| | | |
|---|---|---|
| 3,640,282 A | 2/1972 | Kamen et al. |
| 4,019,499 A | 4/1977 | Fitzgerald |
| 4,167,952 A | 9/1979 | Reinicke |
| 4,417,567 A | 11/1983 | Trick |
| 4,556,050 A | 12/1985 | Hodgson et al. |
| 4,584,990 A | 4/1986 | Haber et al. |
| 4,587,954 A | 5/1986 | Haber |
| 4,994,020 A | 2/1991 | Polyak |
| 5,007,894 A | 4/1991 | Enhorning |
| 5,088,980 A | 2/1992 | Leighton |
| 5,480,434 A | 1/1996 | Eckstein et al. |
| 5,509,888 A * | 4/1996 | Miller ............ A61B 17/12 128/DIG. 25 |
| 5,782,916 A | 7/1998 | Pintauro et al. |
| 5,888,188 A | 3/1999 | Srougi et al. |

(Continued)

*Primary Examiner* — Christine H Matthews
*Assistant Examiner* — Joshua D Lannu
(74) *Attorney, Agent, or Firm* — Davis & Bujold PLLC; Michael J. Bujold

(57) ABSTRACT

A device for wrapping around a bodily organ and preventing overexpansion thereof. The device comprises inner and outer surfaces with a pliant material located therebetween. The inner surface defines a passage and accommodates and reinforces a bodily organ. The bodily organ, following surgical implantation, extends through the passage and is surrounded by the device. The inner surface, in an uncompressed/slightly compressed state, defines a normal state which supports the bodily organ and permits flow of bodily material therethrough. As the bodily organ expands, due to the bodily material flowing therethrough, the inner surface and the pliant material are compressed and, in turn, correspondingly exert a collapsing force, against the outer wall of the bodily organ, which limits and opposes the expansion of the bodily organ and forces the outer wall of the bodily organ back toward its normal state which still permits flow of bodily material through the bodily organ.

15 Claims, 16 Drawing Sheets

(56) References Cited

U.S. PATENT DOCUMENTS

| | | | |
|---|---|---|---|
| 5,893,826 A | 4/1999 | Salama | |
| 6,491,623 B2 | 12/2002 | Snyder et al. | |
| 7,470,228 B2 | 12/2008 | Connors et al. | |
| 7,530,943 B2 | 5/2009 | Lechner | |
| 8,932,200 B2 | 1/2015 | Cotner et al. | |
| 2002/0111530 A1 | 8/2002 | Bakane | |
| 2003/0144575 A1 | 7/2003 | Forsell | |
| 2003/0144648 A1 | 7/2003 | Forsell | |
| 2005/0119674 A1* | 6/2005 | Gingras | A61F 5/0003 606/151 |
| 2006/0167337 A1 | 7/2006 | Forsell | |
| 2008/0045783 A1 | 2/2008 | Forsell | |
| 2010/0160716 A1 | 6/2010 | Snow | |
| 2010/0211092 A1* | 8/2010 | Forsell | A61B 5/076 606/194 |
| 2012/0130157 A1* | 5/2012 | Cotner | A61F 2/0036 600/31 |

* cited by examiner

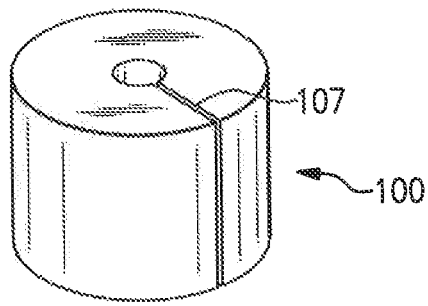
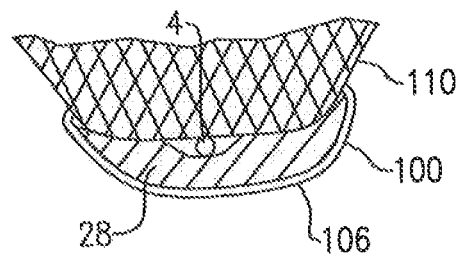
FIG.12A　　　FIG.12B
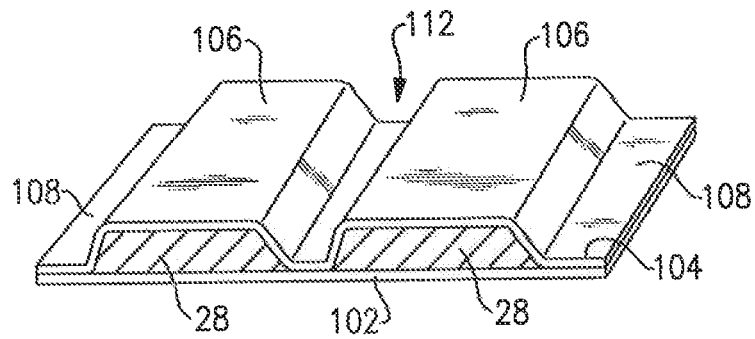
FIG.13
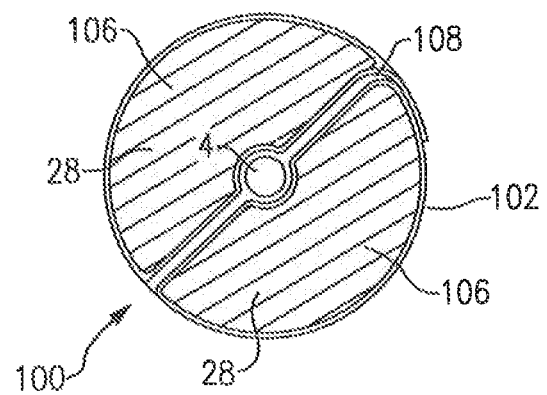
FIG.14

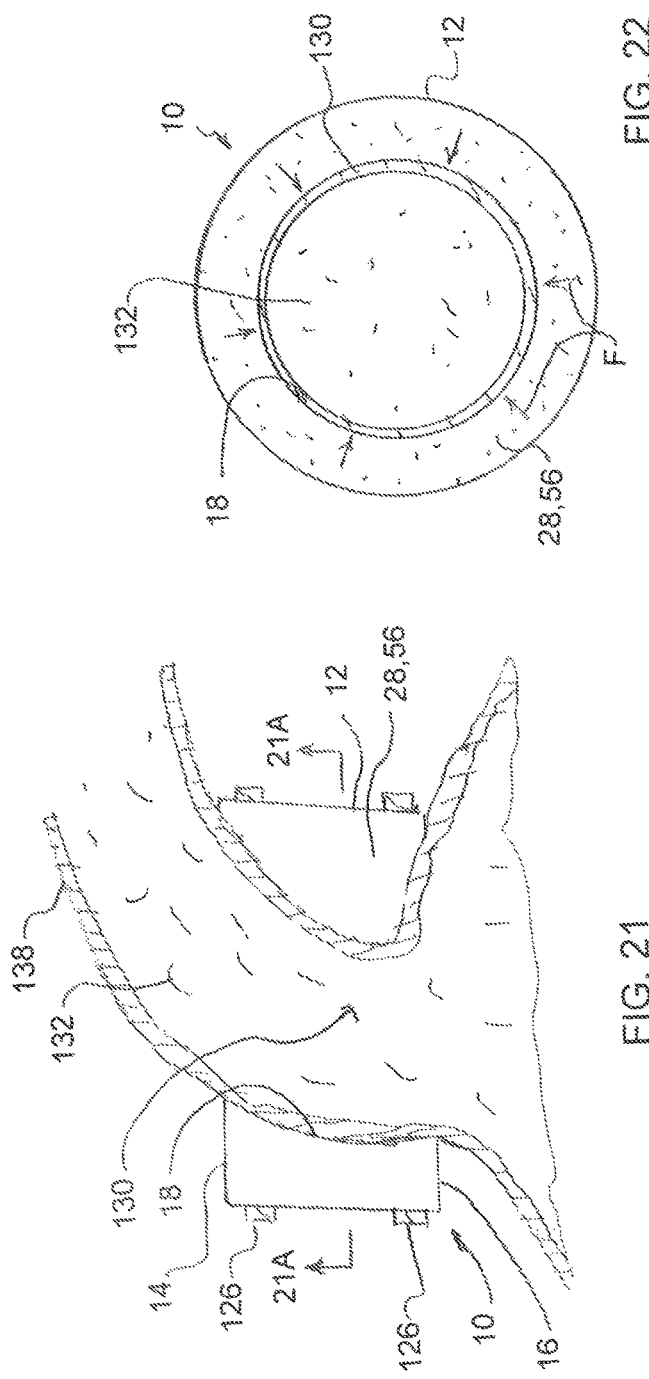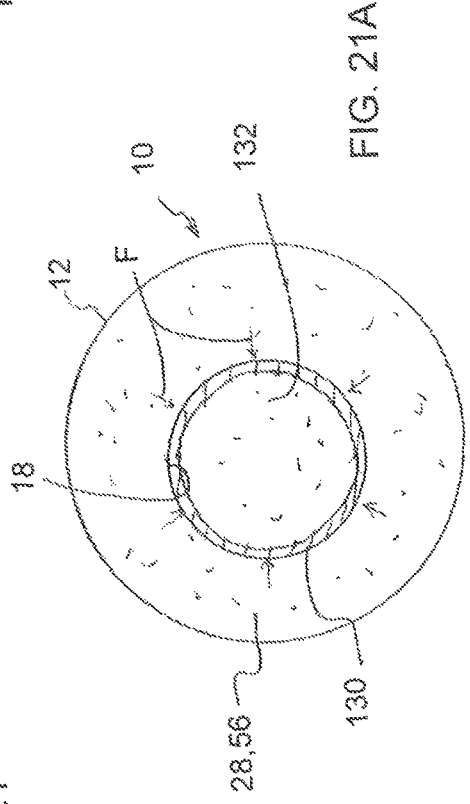

DEVICE FOR PREVENTING OVEREXPANSION OF BODILY ORGAN

FIELD OF THE INVENTION

The present invention generally relates to a device for the treatment of urinary incontinence as well as a variety of other anatomical and physiological processes and/or systems of the human body, such as by circumferentially supporting a thoracic or an abdominal aortic aneurysm, malfunction and/or weakened muscles of the esophagus and/or esophageal sphincter or a stomach so as to prevent excessive or over expansion thereof.

BACKGROUND OF THE INVENTION

Urinary incontinence is a condition found in both males and females and manifests itself such that the bladder, the associated sphincter muscles, prostate gland and/or the urethra malfunctions allowing urine to leak due to the compromise of normal anatomical/physiologic control. Often, urinary incontinence results in the soiling of the person's garments causing emotional, psychological and social issues. As stated, this problem/condition can affect both men and woman; usually exhibited later in life as the urinary tract (system) either weakens or otherwise ceases to properly function due to the natural aging process, stress related to obesity, physical damage or damage due to disease of the urinary system or any of its components and surrounding anatomical structures (prostate, bladder, urethra, musculature, etc.) or secondary to the treatment of diseases such as cancer in and around the area of the urinary system. It is also seen in postpartum or postmenopausal woman that have experienced changes in their uterus, bladder and/or other parts of the urinary system. It is to be appreciated that obesity and "stress incontinence" are often related.

SUMMARY OF THE INVENTION

The device for the treatment of urinary incontinence is a surgically implanted device and is designed to rest against or to circumvent the urethra and/or prostate or some other related anatomical structure(s). The device functions by causing an obstruction to the urethra, i.e., the "urethra non-patent state," so as to interrupt the flow of urine through the urethra or some other related anatomical structure(s). The obstruction can be induced by the application of a constrictive force, a restrictive impediment or sufficient external pressure or force, on or around the urethra so as to collapse and sufficiently close the urethra and/or other structures and thereby maintain the urethra in a non-patent state. That is, the device is shaped, in its normal state, to reconfigure the urethra into the "urethra non-patent state" and thereby overcome the internal system pressure in the urinary tract such that the urethra collapses, constricts, bends or is otherwise reconfigured so that the urine is reliably and consistently prevented from flowing from the bladder through the urethra for discharge from the individual. In addition, such "urethra non-patent state" which collapses, constricts, bends or is otherwise reconfigures the urethra and reliably and consistently prevents the flow of urine, must not be sufficiently great so as to cause any trauma or other permanent harm or damage to the urethra.

When the internal system pressure within the bladder and the urinary tract of the patient increases, a sensory message is transmitted to the brain of the individual that micturition is necessary. A normal systemic function proceeds with the bladder muscles and the abdominal muscles contracting and the bladder sphincter muscle relaxing. This normal systemic function creates an internal system pressure that is sufficiently high enough to overcome the "urethra non-patent state" induced by the device, so that the urethra correspondingly commences to open and thereby permits the flow of urine through the urethra from the bladder, through the device, and out of the body in a normal fashion. The device thus allows for normal urethra patency as the device is forced, by the internal system pressure into the "urethra patent state."

As soon as the internal system pressure of urine in the bladder and flowing along the urinary tract falls below the threshold of the "urethra patent state." the device begins to overcome the internal system pressure caused by the urine flow and naturally and inherently returns back to its "urethra non-patent state" so that the flow of urine subsides and discontinues. That is, the device returns back to its normal state which, in turn, causes the urethra to return back to its non-patent state thereby preventing the flow of urine and an end to the micturition process. This process is inherent to the gradual change in the internal system pressure provided by the anatomical and physiological changes during the micturition process and the mechanical and design parameters of the device whereas the patent and non-patent states are maintained.

It is to be appreciated that there are a variety of different shapes and/or configurations of the device that will allow the device to function in the above manner, i.e., induce a "urethra non-patent state" or "flow obstruction" which will be reconfigurable into a "urethra patent state" or "flow passage" upon experiencing a "sufficient internal system pressure." There may also be features external to a main body of the device which achieve or enhance the efficacy of the device. Examples of such shape configurations and other features will be discussed below as part of the device design.

The device may also be used to support the bladder and other related anatomical structures following the removal of the prostate and the surgical implantation of the device.

The device for treating urinary incontinence according to the invention comprises a body with a laterally outer surface, an inlet end surface, a outlet end surface and an inner surface which defines a passage that extends through the device from the inlet end surface to the outlet end surface. The inlet and outlet surfaces being integral with axially opposite ends of each of the inner and outer surfaces to define an interior of the device. The interior of the device being filled with a medium. The inner surface being movable with respect to the outer surface between a first position and a second position depending on a difference between the desired pressure or force from within the interior of the device and a internal system pressure in the urinary tract such that a diameter of the passage, when the inner surface is in the first position, is smaller than a diameter of the passage when the inner surface is in the second position.

The device may also be used to support the bladder sphincter of a paraplegic who normally uses a catheter to periodically empty the bladder instead of using one which is permanently attached.

As used within this patent application and the appended claims, the term "flow obstruction" is intended to mean that the flow of urine through the urethra is temporarily obstructed, blocked and/or otherwise discontinued due to the device overcoming a sufficiently low internal system pressure in the urinary tract, as a result of relaxed bladder and abdominal muscles and a contracted bladder sphincter muscle, such that the device collapses, constricts, bends, folds or otherwise reconfigures the urethra so that the urine is reliably and consistently prevented from flowing from the bladder and through the urethra.

As use within this patent application and the appended claims, the term "flow passage" is intended to mean that the flow of urine through the urethra is temporarily permitted due to the internal system pressure in the urinary tract becoming sufficiently great, as a result of contraction of the bladder and abdominal muscles and a relaxation of bladder sphincter muscle, such that the urethra overcomes the flow obstruction, e.g., the collapse, constriction, bend, fold or other reconfiguration of the urethra, induced, caused or otherwise created by the device so that the urine can thus reliably and consistently flow from the bladder and through the urethra and, once the internal system pressure in the urinary tract sufficiently decreases, the device is allowed to return to its normal state and induce the "flow obstruction" in the urethra.

As used within this patent application and the appended claims, the term "internal system pressure" is intended to mean the pressure of the urine located within the urinary tract, between the bladder and the device, which is attempting to counteract the flow obstruction induced, caused or otherwise created in the urethra by the device.

As used within this patent application and the appended claims, the term "uncompressed/slightly compressed state of the device" is intended to mean a state in which an inner wall or surface of the device, in either uncompressed or only slightly compressed (by between 0% and 15%, for example) toward the circumferential outer surface of the device, so that the inner wall or surface of the device supports the outer wall of the bodily organ while still permitting the bodily organ to function normally.

As used within this patent application and the appended claims, the term "normal state of the bodily organ" is intended to mean the desired state of the bodily organ which the inner surface of the device is designed to collapse and bias the bodily organ into, i.e., it is the shape of the bodily organ immediately following surgical implantation of the device.

As used within this patent application and the appended claims, the term "bodily material" is intended to mean, either blood, food, water, fluid or any other item/consumable which may be eaten, drank and/or otherwise consumed by an individual, animal or pet.

BRIEF DESCRIPTION OF THE DRAWINGS

The invention will now be described, by way of example, with reference to the accompanying drawings in which:

FIG. 12A is a diagrammatic perspective view of the device according to FIG. 12 wrapped in a cylindrical configuration;

FIG. 12B is a diagrammatic cross sectional view of the device according to FIG. 11 that is implanted to press the urethra against an anatomical feature of a patient;

FIG. 13 is a diagrammatic cross sectional perspective view of another embodiment of the device according to the invention having a planar configuration and multiple shells;

FIG. 14 is a diagrammatic cross sectional view of the device according to FIG. 13 wrapped around the urethra of a patient;

FIG. 21 is a diagrammatic cross sectional view showing the esophageal sphincter being wrapped and supported by the device according to the present invention;

FIG. 21A is a diagrammatic cross-sectional view, along section line 21A-21A of FIG. 21, diagrammatically showing the slight or minimum constrictive force initially generated by the device which biases the esophageal sphincter into its normal flow obstructing condition;

FIG. 22 is a diagrammatic cross-sectional view, similar to section line 21A-21A of FIG. 21, diagrammatically showing the constrictive force generated by the device which opposed expansion of the esophageal sphincter;

DETAILED DESCRIPTION OF THE INVENTION

Figure 1:
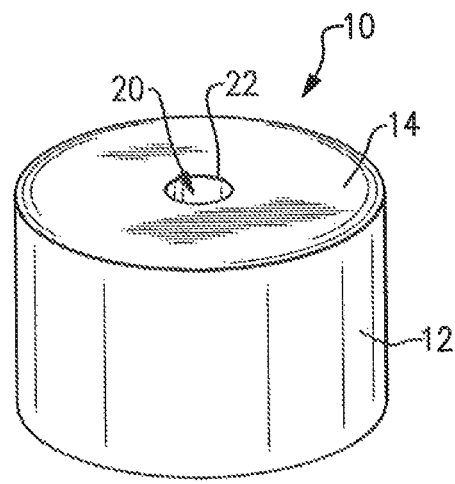
FIG. 1 is a diagrammatic perspective view of an embodiment of the device for the treatment of urinary incontinence, according to the invention, having a single shell.

It is to be appreciated that the device 10 may have a variety of different design configurations, shapes and sizes so as to meet the physiological functional needs/requirements of either male or female patients. Although the device 10 can be utilized in relation to a number of different physiological processes and/or systems, the device 10 will first be generally described below in relation to the treatment of urinary incontinence, and then followed by a few other applications. In this case, the physical shape of the device 10 may take on a variety of configurations, shapes and sizes so as to facilitate normal physiological urinary function and the eliminate urinary leak or incontinence. For this purpose, ideally for the male that has had his prostate gland removed (prostatectomy) or the normal functioning of the bladder, sphincter muscles, urethra and/or prostate gland has been lost due to radiation therapy or any other cause of tissue damage, the device 10 can be formed so as to have the shape of the normal prostate gland. This configuration allows for maintaining the normal bodily function as well as providing support for the bladder that was normally previously provided by the prostate gland, prior to removal thereof due to disease, damage, etc. In this case, the device 10 can also have the shape of a barrel, a marshmallow or a walnut or some other similar or desired shape so as to provide the desired functional results.

The device 10, for the treatment of urinary incontinence, will now be generally described with reference to FIGS. 1 and 2A-2D. As seen in those figures, the urethra 2 extends downward vertically from the bladder 4 and the bladder sphincter muscle 6 and enters and passes through the device 10. The device 10 is vertically aligned and comprises a circumferential exterior or outer wall or surface 12 and opposed inlet and outlet end surfaces 14, 16. The device 10 also has a passage 20 that extends completely through the device 10, from the inlet end surface 14 to and the outlet end surface 16. A radially inwardly facing inner surface 18 of the device 10 defines the passage 20. The urethra 2 is normally accommodated within the passage 20 and extends through and is surrounded by the device 10. The device 10 facilitates reconfiguration of the urethra into the "urethra non-patent state", i.e., creates the flow obstruction, and thereby overcomes the internal system pressure within the urinary tract such that the device 10 collapses, constricts, bends, folds or otherwise reconfigured the urethra 2 so that the urine is reliably and consistently prevented from flowing from the bladder through the urethra.

As mentioned above, the exterior and/or interior shape and dimensions of the device 10 depend somewhat on the physiological functional need/requirement of the patient. In relation to the treatment of urinary incontinence, the device 10 is shaped and dimensioned such that a height of the device 10, i.e., the vertical distance from the inlet surface 14 to the outlet surface 16, is generally preferably in the range of between 0.2 to 5.0 inches, or more preferably between about 0.4 to 3.5 inches. As shown in FIG. 1, the device 10 may be substantially cylindrical with a width of the device 10, i.e., the horizontal distance between opposite lateral sides of the device 10, generally referred to as an outer diameter of the device. The outer diameter of the device 10 is preferably in the range of between about 0.5 to 7.0 inches, or more preferably between about 1.0 to 5.0 inches.

The matriculation process of a patient with the device 10 surgically implanted will now be described with reference to FIGS. 2A-2D. As shown in those figures, the urethra 2 enters an inlet 22, via a first inlet end surface 14 of the device 10, and extends along the passage 20 through the device 10 and eventually exits through the outlet 24 formed in the outlet end surface 16.

Figure 2D:
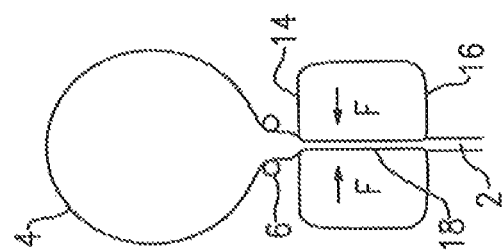
FIG. 2A, 2B, 2C and 2D are diagrammatic cross sectional views of the device of FIG. 1 shown in different positions during the matriculation process.
Figure 2C:
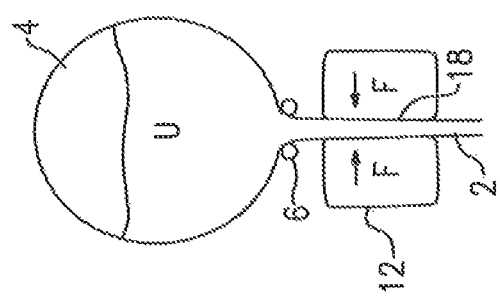

The inner wall or surface 18 of the device 10, which defines the passage 20 through which the urethra 2 passes, is normally compliant, pliable or ductile such that the inner wall or surface 18 can respond to different forces and/or pressures exerted or placed thereon to facilitate either desired flow through the urethra 2 or to cause or induce a sufficient collapse, constriction, bending or other reconfiguration of the urethra, i.e., the flow obstruction, so that the urine is reliably and consistently prevented from flowing from the bladder through the urethra, i.e., the urethra non-patent state. There are generally two opposing pressures or forces that can be applied on and/or by the inner wall or surface 18 of the device 10. In the normal state of the device, as seen in FIGS. 2A and 2D, an external obstruction pressure or force F (such as a constrictive force, a collapse force, bending force, a folding force or some other reconfiguration force) is applied on and/or by the inner wall or surface 18, generally in a radially inward direction as indicated in these figures, by one of a number of different means, so as to exert a force directed at sufficiently reducing the internal dimensions of the passage 20, i.e., create, cause or induce the flow obstruction, and thereby prevent flow through the urethra 2. That is, in the normal state of the device 10, the inner wall or surface 18 is influenced to apply the obstruction pressure or force F radially inward toward and against the urethra 2 so that the diameter of the passage 20 is reduce to a minimum and flow therethrough is prevented. In the urethra non-patent state generally shown in FIGS. 2A and 2D, the inner wall or surface 18 generally collapses the urethra 2 and obstructs flow through the urethra 2 thus preventing the passage of urine U therethrough, i.e., creates the flow obstruction.

Over the course of normal systemic function, the bladder eventually fills with the urine U. When the bladder becomes sufficiently full with the urine U, the abdominal muscles contract and the bladder sphincter muscle 6 correspondingly relaxes, and an internal system pressure (positive pressure) is produced within the bladder 4. The internal system pressure acts upon the urethra 2 and the urethra 2, in turn, counteracts and eventually overcomes the obstruction pressure or force applied thereto by the inner wall or surface 18 of the device 10. Once the internal system pressure of the urine U, contained within the bladder 4 and applied to the internal flow passage of the urethra 2, is greater than the obstruction pressure or force F applied by the inner wall or surface 18 of the device 10, the inner wall or surface 18 of the device 10 is biased sufficiently radially outward so that the urethra 2 thereafter becomes patent, i.e., achieves a "urethra patent state" with a flow passage, and the urine U is thus free to flow along the urethra 2 from the bladder 4 through the device 10 and out of the body in a normal fashion.

Figure 2B:
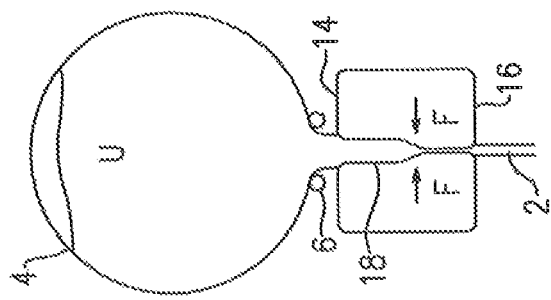
Figure 2A:
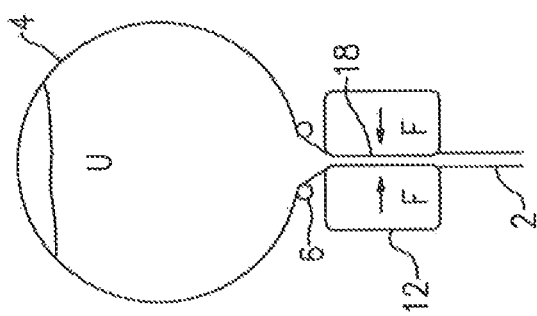

FIG. 2B diagrammatically shows the passage 20 being transformed, by the internal system pressure of the urethra 2, from the urethra fully non-patent state in which the urine U is prevented from flowing from the bladder 4 through the urethra 2 and out of the individual, into the urethra fully patent state, i.e., the passage 20 through the device is being transformed by the internal system pressure to create or cause a flow passage through the urethra 2. FIG. 2C diagrammatically shows the urethra 2 in its fully patent state in which the passage 20 was sufficiently biased radially outwardly, by the internal system pressure of the urethra 2, so that the urine U is relatively free to flow from the bladder 4 through the urethra 2 and out of the individual.

Once the bladder 4 has been sufficiently emptied (FIG. 2D), the bladder muscles and the abdominal muscles again began to relax and the bladder sphincter muscle 6 again begins to constrict which, in turn, reduces the internal system pressure of the urine U flowing along and within the urethra 2. As soon as the obstruction pressure or force F, applied by the inner wall or surface 18 against the urethra 2, becomes greater than the internal system pressure applied by the urine U contained within the urethra 2, the inner wall or surface 18 again gradually transforms back into its normal and inherent configuration or state in which the inner wall or surface 18 again induces, creates or otherwise causes the flow obstruction, e.g., the inner wall or surface 18 constricts, collapses, bends or other reconfigures the urethra 2, and thereby prevents the further passage of urine U therethrough so that the urethra 2 returns back to its non-patent state.

It is to be appreciated that in order to facilitate the desired flow and interruption in flow through the urethra 2, the passage 20 generally needs to be sized, e.g., have a diameter so as to readily accommodate and receive the urethra 2 therein and maintain the urethra 2 in a sufficiently constricted, collapsed, bent, folding or some other reconfigured state when the device 10 is in a normal inherent state while also be able to be sufficiently deformed once the internal system pressure of urine flowing within the urethra 2 overcomes the constrictive, collapsing, bending, folding or some other reconfiguration force of the device 10. It is preferable that the passage 20, in its normal state, has a passage diameter between 0.04 to 2.3 inches, or more preferably a diameter of between about 0.05 to 2.0 inches.

Figure 3:
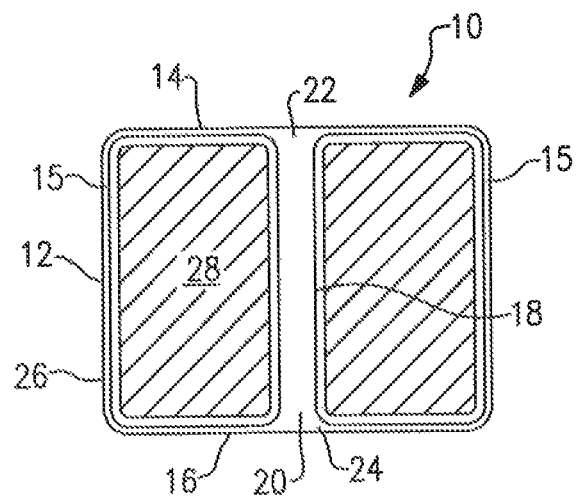
FIG. 3 is a diagrammatic cross sectional view of an embodiment of the device according to the invention having a single shell.

As shown in FIG. 3, the device 10 comprises an exterior sac, pouch or shell 26 which has thin walls that are at least somewhat elastomeric. The sac, pouch or shell 26 can encase a preformed foam body or is sufficiently filled with a foam, a gel, a liquid, a gas or some other generally viscous medium 28. Since the device 10 is to be implanted in the body of a patient, all the materials utilized either for manufacture of or implementation into the device 10 must be bio-compatible. The sac, pouch or shell 26 can be formed from one or more bio-compatible materials such as a radiopaque material, for example. Similarly, the preformed foam body or the foam, gel, liquid, gas or other viscous medium 28 can comprise one or more bio-compatible materials. In one version of this embodiment the sac, pouch or shell 26 surrounds a preformed body which can be made with a bio-compatible foam. The sac, pouch or shell 26 and thus the device 10, in this case, assumes the shape, size and/or configuration of the preformed body which can be formed in a manner discussed below. In another version of this embodiment the sac, pouch or shell 26 is filled with enough foam, gel, liquid, gas and/or other viscous medium 28 such that the device 10 normally assumes the desired shape, size and/or configuration which in this case is at least partly dependent on the constraints of the sac, pouch or shell 26. It is to be appreciated that by adjusting the volume of the foam, the gel, the liquid, the gas and/or the other viscous medium 28 contained within the internal chamber of the device 10, the relative spacing of the opposes inner walls 18 from one another, i.e., the internal diameter of the passage 20, can be correspondingly adjusted, and thus the cross-sectional size of the passage 20 can be customized and fit the specific needs of the individual patient. For example, in the version of the device 10 in which the preformed body is encased within a sac, pouch or shell 26, it is to be appreciated that the constrictive, collapsing, bending, folding or some other reconfiguring force or pressure may be adjusted by injecting a foam, gel, liquid, gas and/or other viscous medium into the sac, pouch or shell 26. In the version of the device 10 in which the sac, pouch or shell 26 is filled with foam, gel, liquid, gas and/or other viscous medium 28, an additional amount of foam, gel, liquid, gas and/or other viscous medium 28 may be introduced into the device 10 to reduce the cross-sectional diameter of the passage 20 and correspondingly increase the constrictive, collapsing, bending, folding or some other reconfiguring force or pressure applied by the device 10 to the exterior surface of the urethra 2. Alternatively, less foam, gel, liquid, gas and/or other viscous medium 28 may be introduced into the device 10 to increase the cross-sectional diameter of the passage 20 and correspondingly decrease the constrictive, collapsing, bending, folding or some other reconfiguring force or pressure applied by the device 10 to the exterior surface of the urethra 2.

As indicated above there are a number of possible ways that the constrictive, collapsing, bending, folding or some other reconfiguring force or pressure may be applied by the device 10 to the exterior surface of the urethra 2. Such constrictive, collapsing, bending, folding or some other reconfiguring force or pressure applied by the device 10 can result from the preformed or molded configuration of the device 10, the shape and/or type of medium that is encapsulated within the bio-compatible bladder and/or by the fact that the outer wall or surface 12 of the device is less pliable, i.e., generally stiffer, relative to that of the inner wall or surface 18 which is in contact with the urethra 2. The outer wall or surface 12 is typically made noncompliant or less pliable than the inner wall or surface 18 by, for example, altering the wall thickness, imparted material properties by any acceptable process, such as laminating the outer wall with another material(s) and/or forming circumferential ribbing 29 around the outer wall 12.

Figure 4:
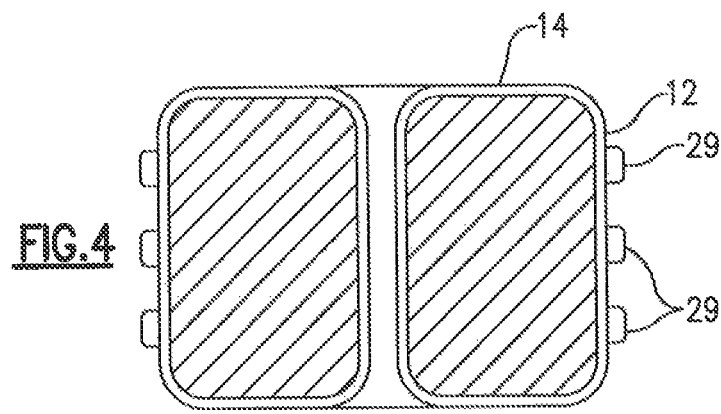
FIG. 4 is a diagrammatic cross sectional view of a further embodiment of the device according to the invention having a single shell.

As shown in FIG. 3, at least one layer 15 is laminated to the outer wall 12 to increase the thickness and reduce the pliancy or pliability of the outer wall 12 with respect to the inner wall or surface 18. In addition, the laminate layer 15 may also partially or completely extend over and cover either, or both of, the inlet and the outlet end surfaces 14, 16 of the device 10. One or more ribs 29, as shown in FIG. 4, can wrap or extend completely around the outer wall 12 of the device 10 to further increase the rigidity and/or reduce the pliancy or pliability of the outer wall 12. With such a design, the outer wall 12 will be more resistant to changes in pressure or force, which occur within the device 10, so that all such resulting pressures or forces of the device 10 are generally directed radially inwardly toward the inner wall 18 which interacts with the urethra 2.

Figure 5A:
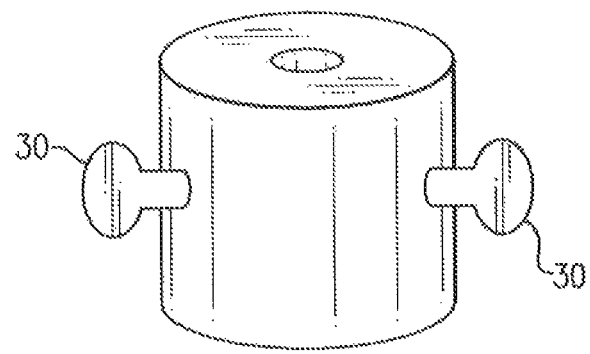
FIG. 5A is a diagrammatic perspective view of an embodiment of the device according to the invention having reservoirs.
Figure 5B:
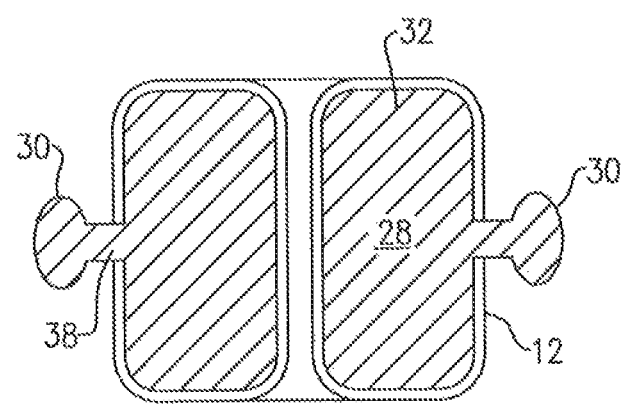
FIG. 5B is a diagrammatic cross sectional view of the embodiment of the device according to FIG. 5A.

As diagrammatically shown in FIGS. 5A and 5B, the device 19 may include two or more "ears", pouches or reservoirs 30 that are secured to and extend from the outer wall 12 of the device 10. The reservoirs 30 are more pliable than the outer wall 12 of the device 10 and may simply allow for the flow or transfer of the foam, gel, liquid, gas and/or other viscous medium 28, normally contained within an internal chamber 32 of the main body of the device 10, when the internal system pressure forces or biases the inner wall 18, which is in contact with the urethra 2, normally radially outward thereby increasing the pressure or force within the internal chamber 32 of the main body. This increase in pressure or force within the internal chamber 32 is relieved by permitting the flow of the displaced foam, gel, liquid, gas and/or other viscous medium 28 to one or both of the reservoirs 30. For this purpose alone, the reservoirs 30 would require little or possibly no pressure to inflate. The reservoirs 30 may simply receive the displaced foam, gel, liquid, gas and/or other viscous medium 28 and then normally return the displaced foam, gel, liquid, gas and/or other viscous medium 28 back to the device 10 once the inner wall 18 of the device 10 returns back to its normal state as the internal system pressure in the urinary tract gradually diminishes. The reservoirs 30 may also serve as a pressure or force control for the device 10 by forcing the medium 28 back into the device 10 in the event that the reservoir(s) 30 stretches when receiving the displaced foam, gel, liquid, gas and/or other viscous medium 28. This is opposed to the reservoir 30 simply receiving or taking up the medium.

Figure 6A:
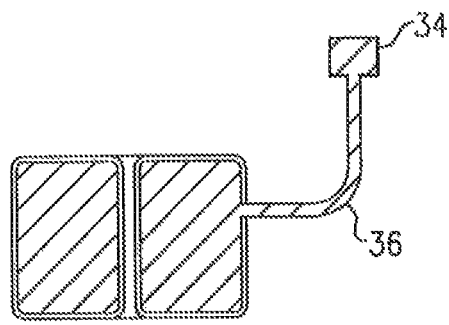
FIGS. 6A, 6B, 6C are diagrammatic cross sectional views of an embodiment of the device having different pressure controls and/or attachment means.

As shown in FIG. 6A, one or more remote reservoirs 34 may be connected or otherwise coupled to the interior chamber of the device 10 via a tube 36, with the remote reservoirs 34 being located at a distance from the device 10, instead of being fixed to and supported by the outer wall 12, as with the embodiment shown in FIGS. 5A and 5B. In either case, the opening 38 or the tube 36, coupled between the internal chamber of the main body 32 and the reservoir 30 or 34, may be used to control the flow of the medium within the sac, pouch or shell 26 thus providing a method of gradually releasing and applying an external pressure or force within the sac, pouch or shell 26 on the inner wall 18 of the device 10 and the urethra 2.

Figure 6B:
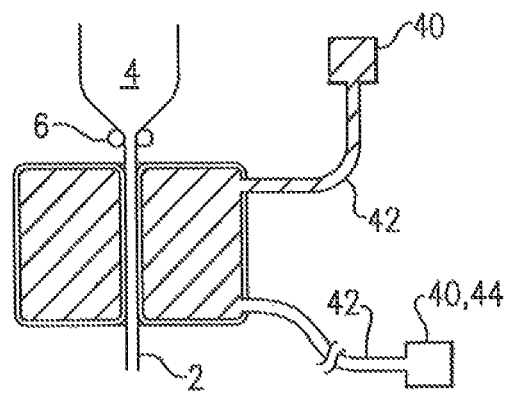

In a further embodiment shown in FIG. 6B, a manual pressure or force control device 40 can be coupled to the device 10, via a conduit 42, to facilitate manually controlling the pressure or force within the sac, pouch or shell 26 on the inner wall 18 and the urethra 2. The manual pressure or force control device 40 may be located and spaced from the outer wall 12 of the device 10, adjacent to the sac, pouch or shell 26, at any physiologically sufficient location within the body cavity of the patient, or even possibly external to the body cavity, or possibly within the scrotum.

An external pressure control 44 (EPC) can be attached to the device 10, via a conduit 42, to mechanically control the pressure within the sac, pouch or shell 26 and thereby the obstruction pressure or force exerted on and/or by the inner wall 18 against the outer surface of the urethra 2. The external pressure control 44 may be mechanically manipulated such that actuation, in a first direction, increases the internal pressure within the sac, pouch or shell 26 while actuation in a second opposite direction reduces the internal pressure within the sac, pouch or shell 26. The external pressure control 44 can be located remote from the device 10, either in the scrotum or possibly external of the body cavity.

The sac, pouch or shell 26 of the device 10 may also be made of a self sealing material which accepts a hypodermic needle and suitably self seals itself once the hypodermic needle is removed from the device 10. Such a sac, pouch or shell 26 would facilitate adjustment of the pressure or force within the sac, pouch or shell 26 and thus the pressure or force exerted by the inner wall 18 against the outer surface of the urethra 2. In this manner, the volume of foam, gel, liquid, gas and/or other viscous medium 28, and thus the pressure or force within the internal chamber, can be readily adjusted at any time, even once the device 10 is surgically implanted within the patient.

Further, the sac, pouch or shell 26 of the device 10 may be impregnated with an applicable pharmaceutical material(s) so as to be drug-eluting for (but not limited to) the purpose of preventing infection or stone build up at the surgical site or anastomosis and maybe radiopaque for radiological evaluation.

Figure 6C:
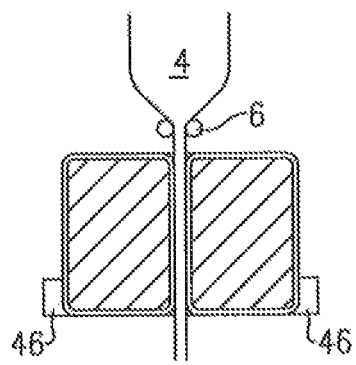

The device 10 may also contain external features to facilitate locating and securing of the device via the surgical procedure. External tabs or other features 46 that are designed to accept sutures, staples or any other conventional and accepted surgical apparatus may be used to simply hold the device 10 in place in the desired location on and/or around the urethra 2 (see FIG. 6C, for example). The device 10 may also be held in a sling like fashion in such a position that the device 10 applies a generally vertically upward force on the bladder 4 for supporting the bladder 4. Alternatively, a band, a wrap or a belt may be used to increase the obstruction pressure or force that the device 10, e.g., the inner wall 18, transfers or imparts on to the exterior surface of the urethra 2 and such band, wrap or belt may be secured in place by means of one or more sutures and tabs 46.

Figure 7:
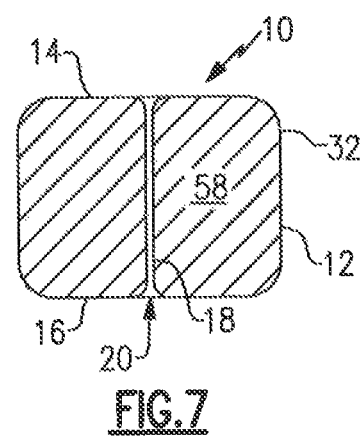
FIG. 7 is a diagrammatic cross sectional view of another embodiment of the device according to the invention formed without a shell.

As generally shown in FIG. 7, the device 10 may be manufactured from a foam, a gel or some other viscous material 58. This embodiment of the device 10 differs from the previous embodiments in that this device 10 does not comprise a sac, pouch or shell 26. That is, the foam, gel or other viscous material 58 is preformed, molded, cut or otherwise processed to have a specific shape, size and/or configuration. The foam, gel or other viscous material 58 is selected such that the device 10 is inherently compliant or pliable while, at the same time, the device 10 is sufficiently resilient. These characteristics allow the device 10 to retain the desired shape, size and/or configuration as well as normally induce the desired flow obstruction in the urethra 2, due to the shape, diameter or contour of the inner surface 18, while, at the same time, the device 10 is partially deformable so as to permit the desired flow of the urine through the urethra 2.

According to this embodiment, the device 10 comprises a preformed body 32 made of the foam, gel or other viscous material 58. In this embodiment, the device 10 comprises a circumferential outer surface 12 and inlet and outlet end surfaces 14, 16. The device 10 also has a radially inner surface 18 which defines a passage 20 that extends through the device 10 between the inlet and the outlet surfaces 14, 16. This embodiment of the device 10 generally functions in the same manner as described above. The foam, gel or other viscous material 58 that forms the device 10, in this case, is one or more bio-compatible materials, As noted above, the preformed body 32 of the device 10 has a specific predetermined shape or form which is chosen to support any desired body part and also provide the desired flow obstruction in the urethra 2. In one embodiment, the device 10 is a single piece which has been formed into a generally "doughnut" shaped configuration. The device 10 has a central passage 10 that extends vertically completely the device 10 and the urethra 2 must be threaded through device 10 during the implantation procedure, e.g., the urethra is first cut and then reconnected to itself or possibly reconnected to a base of the bladder 4.

It is to be appreciated that the passage 20 may have a variety of different arrangements and configurations which all provide suitable flow obstruction of the urethra 2 so as to prevent the flow of fluid therethrough. For example, the inner wall or surface 18 of the device 10 that defines the passage 20 may be configured so as to be smooth, fluted, ribbed, spiral or knobby. In addition, the shape, diameter and/or contour of the wall or surface 18 may vary as long as the passage 20 induces the desired flow obstruction in the urethra 2, e.g., provides the proper pressure/flow relationship. The passage 20 may be straight, non-linear, curved, hour glass shaped or conical in either direction. It should be appreciated that the passage 20 is not limited to the specific configurations described herein.

Figure 8:
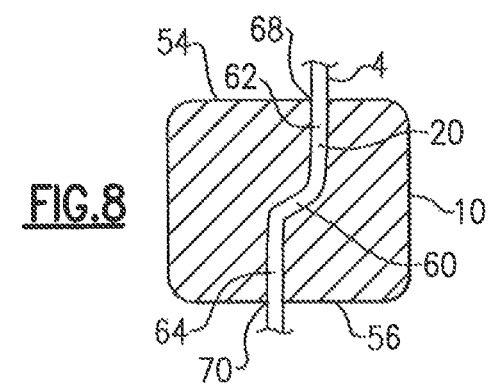
FIG. 8 is a diagrammatic cross sectional view of the device according to FIG. 7 formed without a shell and having a different passage configuration.
Figure 9:
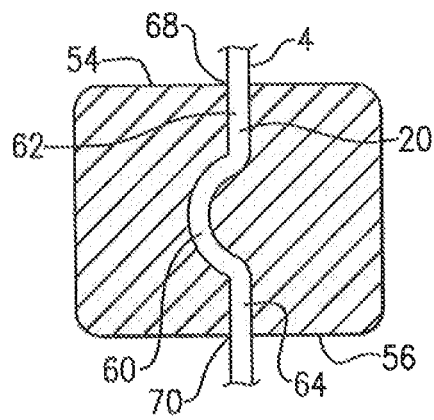
FIG. 9 is a diagrammatic cross sectional view of the device according to FIG. 7 formed without a shell and having another distinctive passage configuration.

A couple examples of the device 10 having a non-linear passage 20 for creating or inducing the desired flow obstruction are generally shown in FIGS. 8 and 9. The devices 10, as illustrated in those figures, comprise a generally centrally located passage 20 which extends vertically from an inlet end surface 54 of the device 10 to an outlet end surface 56 of the device 10. At one location between the inlet end surface 54 and the outlet end surface 56 of the device 10, the passage 20 includes a deviation 60 which causes, induces or creates the flow obstruction. As used herein the term deviation relates to a change in the axial path or course of the passage 20 as the passage extends through the device 10 from the inlet end surface 54 to the outlet end surface 56. The respective deviation 60, in each of these devices 10, is generally located centrally between the inlet end surface 54 and the outlet end surface 56 of the device 10, however, it is to be appreciated that the deviation 60 could be located any where between the inlet end surface 54 and the outlet end surface 56 of the device 10 and possibly two or more deviations 60 may be provided along the passage 20.

The deviation 60 in the device 10, shown in FIG. 8, is such that the axial path of an upper portion 62 of the passage 20 is offset from an axial path of the lower portion 64 of the passage 20, e.g., two bends or turns are provided therein. In such case, the passage inlet 68 in the inlet end surface 54 of the device 10 is vertically offset from a passage outlet 70 in the outlet end surface 56 of the device 10.

The deviation 60 shown in FIG. 9 is such that the path of the upper portion 62 of the passage 20 is axially aligned with the path of the lower portion 64 of the passage 20. As such, the passage inlet 68 in the inlet end surface 54 of the device 10 is also axially aligned with the passage outlet 70 in the outlet end surface 56 of the device 10. The deviation 60, which causes, induces or creates the flow obstruction in this embodiment of the device 10, is a "jut." That is, the passage 20 juts horizontally to one side before jutting horizontally back in such a manner that the upper and lower portions 62, 64 and the passage inlet and outlet 68, 70 of the passage 20 are substantially axially aligned with one another.

The physical characteristics of the foam, gel, liquid, gas and/or other viscous medium or material 58, used in the embodiments shown in FIGS. 7-9, are such that the medium or material 58 will allow for the device 10 to be pliable, so as to permit the desired flow through the urethra 2, and, at the same time, sufficiently resilient so as to return back to its initial shape and provide the desired flow obstruction in the urethra 2. With these characteristics, the device 10, or more specifically the shape of the device 10, will be able to conform to forces e.g. internal system pressures placed thereon and when these forces are discontinued or removed, the device 10 will normally return back to its originally manufactured shape. In this manner, changes in system pressure gradients and the flow of fluid through the passage 20 will cause the desired changes in the shape of the device 10 or more specifically the diameter of the passage 20 of the device 10. Furthermore, the device 10 will have the ability to maintain a specific design shape over an extended period of time as required.

Figure 10:
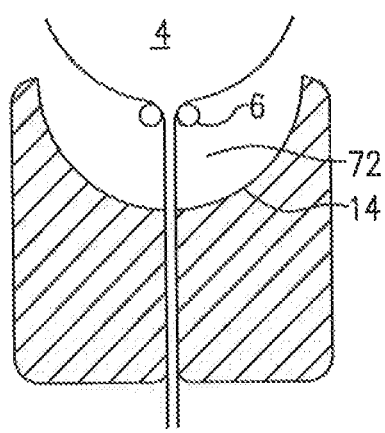
FIG. 10 is a diagrammatic cross sectional view of the device according to FIG. 7 having a void for supporting the bladder or adjacent tissue of a patient.

As shown in FIG. 10, in order to address the issue of excessive trauma to the anastomosis by the device 10 itself, the inlet end surface 14 of the device 10 may be configured to include a cavity 72 where the device 10 would generally contact the affected area of the body of the patient, e.g., a base of the bladder 4. As shown, the cavity 72 is a cup shaped surface or depression formed in the inlet end surface 54 of the device 10 that provides little or no contact with the anastomosis while still providing some support for the bladder 4 and enhancing placement of the device 10 within the patient.

Figure 11:
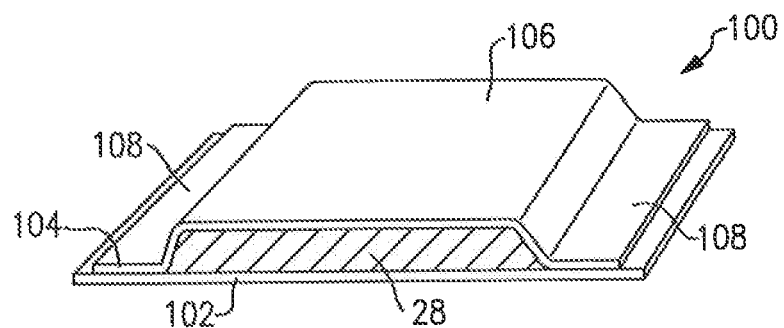
FIG. 11 is a diagrammatic cross sectional pictorial view of a further embodiment of the device according to the invention having a planar configuration.

Another embodiment of the device 100, as shown in FIG. 11, comprises a generally planar base layer 102 and top layer 104 that is bonded to the base layer 102 in such a manner that a shell or pocket 106 is formed between the base and top layers 102, 104 and the shell or pocket 106 extends axially along the length of the device 100. Similar to the embodiment described above, the shell or pocket 106 is filled with foam, gel, liquid, gas and/or some other viscous medium 28. In this embodiment, the shell or pocket 106 is generally a planar elevation, ridge or strip that extends along the length of the device 100. The outer side edges 108 of the device 100, i.e., the sides of the device 100 that are opposite one another, extend lengthwise of the device 10 and do not include the shell or pocket 106. That is, the outer side edges 108 of the device 100 only comprise the top and base layers 102, 104 and not the shell or pocket 106 or any of the foam, gel, liquid, gas or some other viscous medium 28.

Both the base and the top layers 102, 104 of the device 100 are sufficiently compliant and pliable with the top layer 104 being more compliant in comparison to the base layer 102. The greater compliancy of the top layer 104 enables the top layer 104 to move relative to the base layer 102 depending on the internal system pressures applied thereon.

In the manner described above, the top layer 104 will generally be biased away from the base layer 102, when the pressure within the shell or pocket 106 increases and, conversely, toward the base layer 102 when the pressure within the shell or pocket 106 decreases or when the internal system pressure is acting on the shell or pocket 106. The differences in compliancy, between the base and the top layers 102, 104, can be achieved by a difference in the thickness of the two layers with the base layer 102 being thicker than the top layer 104. The differences in the types and/or kinds of materials which form the base and the top layers 102, 104 can also cause differences in the compliancy of the two layers. In this manner, the top layer 104 is formed by a material that is more compliant than the material which forms the base layer 102.

Figure 12:
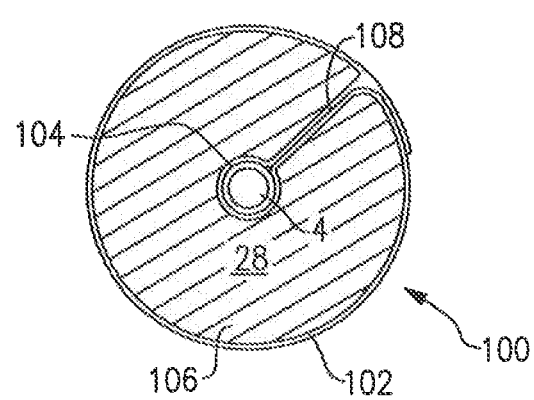
FIG. 12 is a diagrammatic cross sectional view of the device according to FIG. 11 wrapped around the urethra of a patient.

When this embodiment of the device 100 is implanted in a patient, the device 100 is wrapped around the urethra 2 and the two opposed outer ends 108 are bonded or otherwise permanently connected together via an adhesive, ultrasonic welding or any other surgically acceptable or conventional means (FIG. 12). In this case, the device 100 is in the general form of a sleeve which surrounds and normally applies a desired radially directed pressure or force on the exterior surface of the urethra 2 which is suitable to temporarily obstruct the flow of urine through the urethra 2. It is to be appreciated that the two opposed side edges 108 of the device 100 could be bonded with one another, before the device 100 is surgically implanted, but this method of implanting the device 100 would require the urethra 2 to be severed and then reconnected, which is typically less desirable. As with the previously described devices, the urethra 2 would extend axially through the device 100 and provide the desired flow obstruction and flow passage for the urethra 2, as described above.

As shown in FIG. 12B, the device 100 may be utilized in the generally planar configuration shown in FIG. 11. In this planar configuration, the device 100 is implanted such that the urethra 2 is located between the top layer 104 of the shell or pocket 106 of the device 100 and some other anatomical structure 110, e.g., a pelvic bone, muscle, etc., so as to provide the desired flow obstruction in the urethra 2 by collapsing, constricting, sandwiching or otherwise crimping the urethra 2, between the shell or pocket 106 of the device 100 and the anatomical structure 110 as well as allow the desired flow passage upon suitable deformation of the top layer 104 of the device 100 and thereby continue to allow for normal function of the urinary tract.

FIGS. 12 and 12A show a modified version of the device 100 in which the device 100 generally has a cut or slit 107 that extends from an outer wall radially inwardly toward the passage 20 and along the entire length of the device 100. According to this embodiment, during the surgical procedure, the slit 107 is separated so as to facilitate placing the device 100 around the urethra 2 whereby thereafter the urethra 2 is completely accommodated within the passage 20. This embodiment avoids having to cut or otherwise sever the urethra 2. As with the previous embodiments, one or more rib(s) or other circumferential element(s) can wrap or extend completely around the outer wall or surface of the device 100 to maintain the slit 107 in the substantially closed position.

In a similar embodiment, as shown in FIG. 13, the device 100 may comprise two or more shells or pockets 106 each filled with the selected foam, gel, liquid, gas and/or other viscous material or medium 28. This embodiment of the device 100 is similar to the preceding embodiment in that the device 100 comprises a generally planar a base layer 102 and a top layer 104 that is bonded to the base layer 102. However, according to this embodiment the top and the base layers 104, 102 are bonded to one another at three different locations along the width of the device 100 so as to form two or more separate shells or pockets 106, e.g., generally planar elevations, ridges or strips that extend axially along the length of the device 100. Each shell or pocket 106 is each filled with a foam, gel, liquid, gas and/or some other viscous medium 28. By bonding or otherwise securing the top layer 104 to the bottom layer 102 at a number of locations along the width of the device 100, one or more troughs 112 are formed between the shells or pockets 106 and likewise extends along the length of the device 100.

As previously described above, the device 100 can be implanted by either wrapping the device 100 around the urethra 2 or connecting and the device 100 to another anatomical structure, as described above. When the device 100 is wrapped around the urethra 2, the outer side edges of the device 100 are bonded together via an adhesive, ultrasonic welding or any other surgically acceptable or conventional means. In this case, the device 100 is in the general form of a sleeve, as shown in FIG. 14, which surrounds and applies a suitable force or pressure to the exterior surface of the urethra 2 and thereby provides the desired flow obstruction which prevents urine from flowing along the urethra 2. The urethra 2 passes through the device 100 and is sandwiched or clamped between the two or more mating pairs of shells or pockets 106.

FIGS. 14A, 14B, 14C, 14D are diagrammatic cross sectional illustrations of the device 100 having two or more separate shells or pockets 106 that have been partially wrapped around the urethra 2 and sandwich or otherwise accommodate the urethra 2 therebetween. That is, each one of the two or more separate shells or pockets 106 combined with one another to generally form a cylindrical or sleeve like configuration which totally surrounds and encloses the urethra 2. As with the previous embodiments, one or more rib(s) or other circumferential element(s) can wrap or extend completely around the outer wall or surface of the device 100 to maintain the slit 107 in the substantially closed position.

Figure 14A:
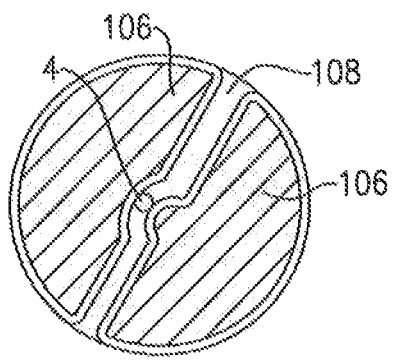
FIGS. 14A, 14B, 14C, 14D are diagrammatic cross sectional views of the device, according to FIG. 13, wrapped around the urethra of a patient and having various shell configurations.
Figure 14B:
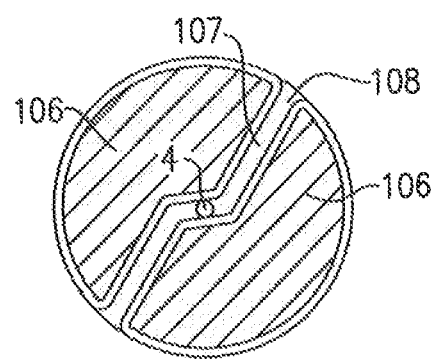
Figure 14C:
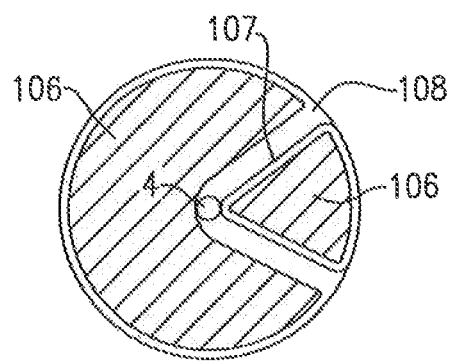
Figure 14D:
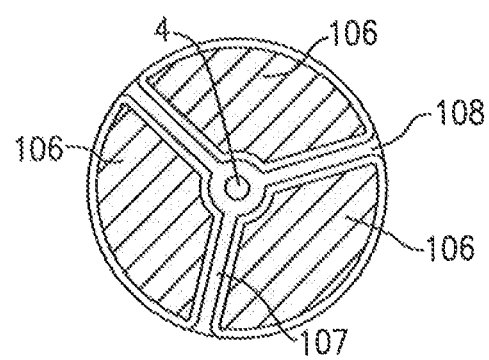

The top layer 104 of the shells or pockets 106 can be formed having specific features so as to provide the device 100 with different cross sectional configurations, for example. The shells or pockets 106 and device 100 can have a simple clam shell configuration, with or without a passage, as shown in FIG. 14. A passage and tab (or notch and key) configuration is shown in FIG. 14A. The shells or pockets 106 and the device 100 can be configured to include a passage formed by mating sides, as shown in FIG. 14B, or a V-shaped passage, as shown in FIG. 14C. FIG. 14D shows a configuration with multiple chambers.

Figure 15A:
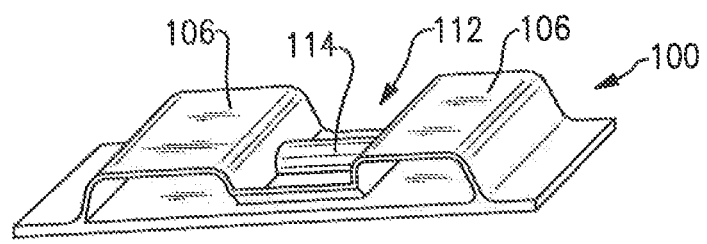
FIG. 15A is a diagrammatic cross sectional perspective view of the device, according to FIG. 13, with a conduit extending between the two shells.
Figure 15B:
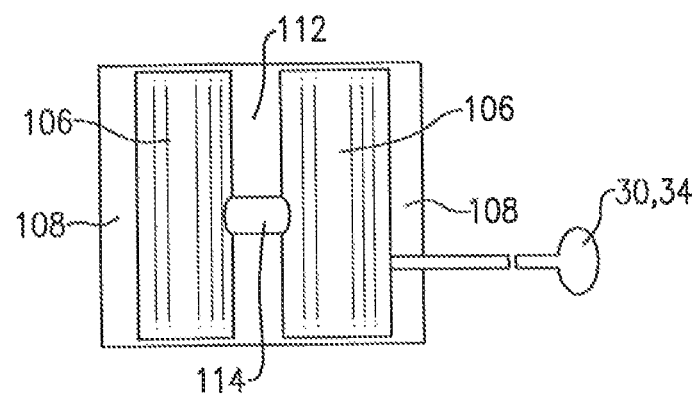
FIG. 15B is a diagrammatic top plan view of the device, according to FIG. 13, with a conduit extending between the two shells and having a reservoir for adjusting the pressure of the shells.

It is possible in the embodiments of the device 100 formed with two or more shells or pockets 106 that the shells or pockets 106 can be either independent of another or one or more of the individual chambers 106 may be connected with one another by a conduit 114 such that the foam, gel, liquid, gas and/or some other viscous medium 28 can readily pass and flow therebetween, as diagrammatically shown in FIGS. 15A and 15B. Further, these embodiments of the device 100 can also comprise "ears," pouches or reservoirs 34 which function, as previously described above.

Figure 16B:
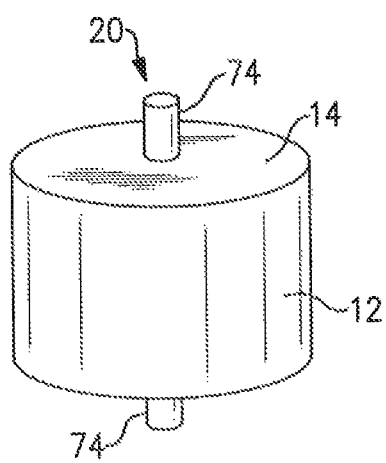
FIG. 16B is a diagrammatic perspective view of the device according to FIG. 16A.
Figure 16A:
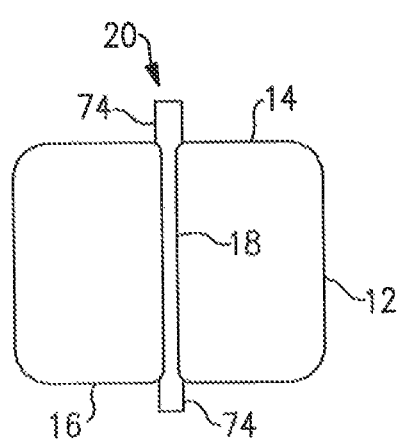
FIG. 16A is a diagrammatic cross sectional view of an embodiment of the device with an inlet and an outlet neck for anastomosing the urethra to the device.

FIGS. 16A and 16B illustrate another embodiment of the device 10 which includes a protruding inlet and/or outlet neck or collar 74. During surgical implantation of the device 10, the neck or collar 74 facilitates anastomosizing of the urethra 2 to the device 10. In one example of this embodiment, the neck or collar 74 is formed by an extension of the inner wall 18 of the device 10. As seen in FIG. 16A, the inner wall 18 of the device 10 extends a desired distance from both the inlet and the outlet end surfaces 14, 16 of the device 10. The neck or collar 74 of the device 10 can be modified, i.e., either shortened or lengthened, depending on the specific requirements of the patient. Implantation of this form of the device 10 requires that the urethra 2 be cut or severed. Once the device 10 has been located within the patient the severed ends of the urethra 2 are sutured or otherwise connected to the necks or collars 74 of the device 10 in a known manner.

It should be recognized that although the device has been described herein as a device for treating urinary incontinence, the device could be resized and reconfigured to treat or augment the function of other anatomical or physiological abnormalities or anomalies which compromise the pressure and/or a flow and which require corrective measures to ensure proper anatomical or physiological function to an organ, system or body. Any form of aneruism or herniation or weakening of any conduit within the body, whether it be fludic, gascous or semisolid or solid in nature within the body. The device may be used to correct or treat deficiencies and/or insufficiencies such as: esophageal/gastric hiatus herniation or gastroesophageal reflux disease (GERD). The device may be configured as a laparoscopic adjustable gastric encompassing wrap or clamp for the treatment and/or correction of obesity in bariatric patients, as discussed below. Further, the device could be configured to treat or support arterial or venous aneurysms (vascular aneurysms) as discussed below. Still further, the device may be configured to treat and/or repair anatomical eventrations such as herniation of the intestines. The device could be configured to replace or augment organs or tissues which function to transfer air, fluids or solids by controlling and regulating pressure and/or flow, e.g., colon, rectum, sphincters, etc. Any time an anatomical sphincter requires support in form and/or function and/or needs replacement, the device can be configured to correct, augment and/or treat a variety of herniations and vericosities.

Turning now to FIGS. 17-19B, another embodiment of the present invention will now be now be described in detail. Since this embodiment is somewhat similar in design and function to the previously discussed embodiments, similar or like elements are given the same reference numerals.

Instead of the device 10, according to this and the following additional embodiments, initially providing a constricting function as described above, the device is designed to normally support the exterior wall of the bodily organ, and permit flow therethrough, and only generate or provide a constricting force when the organ attempts to expand, so as to prevent excessive or overexpansion of the bodily organ. That is, the device 10 and is designed to enclose, encase and/or wrap around the bodily organ and permit the bodily organ to function generally in its normal operating condition, allow fluid/material to flow therethrough and also permit limited expansion thereof while generating a contraction force which opposes the expansion of the bodily organ and assists with returning the bodily organ back to its desired operational configuration. Following surgical installation, the device 10 completely surrounds the bodily organ and is arranged and designed to permit "normal" operation of the bodily organ while preventing excessive or overexpansion of the bodily organ.

Figure 17:
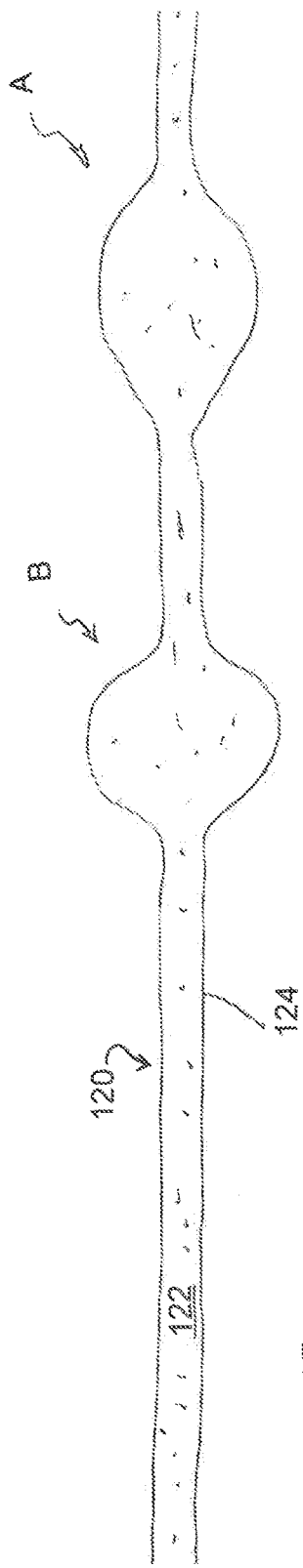
FIG. 17 is a diagrammatic cross sectional view of a portion of an artery showing both a thoracic/fusiform aortic aneurysm (see area A) and an abdominal/sacular aortic aneurysm (see area B)

The bodily organ, diagrammatically shown in FIG. 17, is a portion of an artery 120 through which blood 122 flows from the heart for distribution to other organs and areas of the human body. As it is conventional, a normal functioning artery 120 has an outer diameter of about 1 cm but such artery 120, during normal operation while pumping blood 122 from the heart, may possibly expand to 1.5 cm to 3 cm, as the blood pressure within the artery 120 increases, due to various reasons. In addition, the outer diameter of such artery 120, during normal operation while pumping blood 122 from the heart, typically decreases back to a diameter of approximately 1.0 cm, as the blood pressure within the artery 120 eventually decreases. However, is well known in the art, as an individual ages, platelets and other compositions tended to accumulate or built up on the inner wall of an artery 120 and such build up may possibly result in a thoracic/fusiform aortic aneurysm (see area A of FIG. 17) or an abdominal/sacular aortic aneurysm (see area B of FIG. 17), e.g, excessive or overexpansion of the artery 120. In either event, there is an increased propensity for the inner surface of such weakened section of the artery 120 to eventually become sufficiently clogged or blocked so that the internal blood pressure increases, within the artery 120, and excessively stretches and/or expands the artery wall 124 thereby causing a rupture thereof. Such rupture, in turn, leads to internal bleeding which, in many instances, results in a catastrophic event for the individual whose ruptured, e.g., an aneurysm.

One conventional technique for attempting to address this problem is to position an internal stent (not shown) within each problematic area of the artery 120, e.g., in areas A or B of FIG. 17). However, this technique tends to compound the problem since platelets and other bodily compositions, naturally flowing along with the blood 122, have a tendency to accumulate gradually on the exterior surface of the stent and, over time, may possibly lead to eventual blockage of the artery 120. While various coatings, applied to the exterior surface of the stent, tend to minimize accumulation of platelets and other compositions on stent, such coatings generally somewhat have limited success.

As shown in FIGS. 18, 18A, 18B and 18C the present invention is directed at providing support circumferential around the weakened section of the artery 120 and thereby prevent excessive or overexpansion of the artery 120. As generally shown in these Figures, the device 10 is designed, e.g., size and shaped, so as to completely surround the weakened section of the artery 120 and provide support thereto which opposes and counteracts further radial expansion of the artery 120. Typically, as shown, the device 10 has an axial length that is longer than the axial length of the weakened section of the artery 120 so that the device 10 partially overlaps, on both opposed axial ends thereof, non-weakened, normal functioning sections of the artery 120. While the extent of the overlap of the non-weakened, normal functioning sections of the artery 120 on each opposed end of the device 10 can vary from application to application, it is preferred that the overlap range somewhere between 0.25 cm and about 2 cm, and more preferably about 1 cm.

As with the previous embodiment, the device 10 has a central passage 20 that extends completely axially through the device 10, from the inlet end surface 14 to and the outlet end surface 16. A radially inner surface 18 of the device 10 defines the passage 20 and this radially inner surface 18 of the passage 20 is designed, during use, to directly engage with the outer wall of the artery 120 and thereby sightly bias, constrict and/or force the outer wall of the artery 120 radially inwardly so as to decrease slightly the diameter of the artery 120, but without significantly obstructing the flow of blood 122 through the artery 120 and/or significantly increase the pressure of the blood 122 flowing along the artery 120. Alternatively, the radially inner surface 18 of the passage 20 may possibly be slightly space from the exterior wall of the artery 120, e.g., by 0.05 mm-0.3 mm for example.

That is, the weakened section of the artery 120 is normally accommodated within the passage 20 and completely surrounded by the inner surface so that the device 10 supports the weakened section of the artery 120. It is important to note that according to this embodiment, which is different from the previous embodiments, the radially inner surface 18 of the passage 20 is not designed, in its substantially uncompressed state, to constrict or prevent the flow of fluid through the artery 120. To the contrary, the device 10 wraps around and completely surrounds the artery 120 and is designed to support and prevent excessive and/or overexpansion of the artery wall 124. That is, as the artery wall 124 attempts to expand further, i.e., attempts to increase in diameter as the blood pressure inside the artery 120 increases, the artery wall 124 must also force the radially inner surface 18 of the passage 20 radially outwardly and thereby compress the pliant material 28, 56, located between the inner surface 18 and the outer surface 12 of the device 10. Such compression of the pliant material 28, 56, in turn, provides resistance to expansion of the artery wall 124 which helps distribute the increased blood pressure to other non-weakened areas or sections of the artery 120 and thereby avoids a potential rupture of the weakened, reinforced wall of the artery 120.

Figure 18:
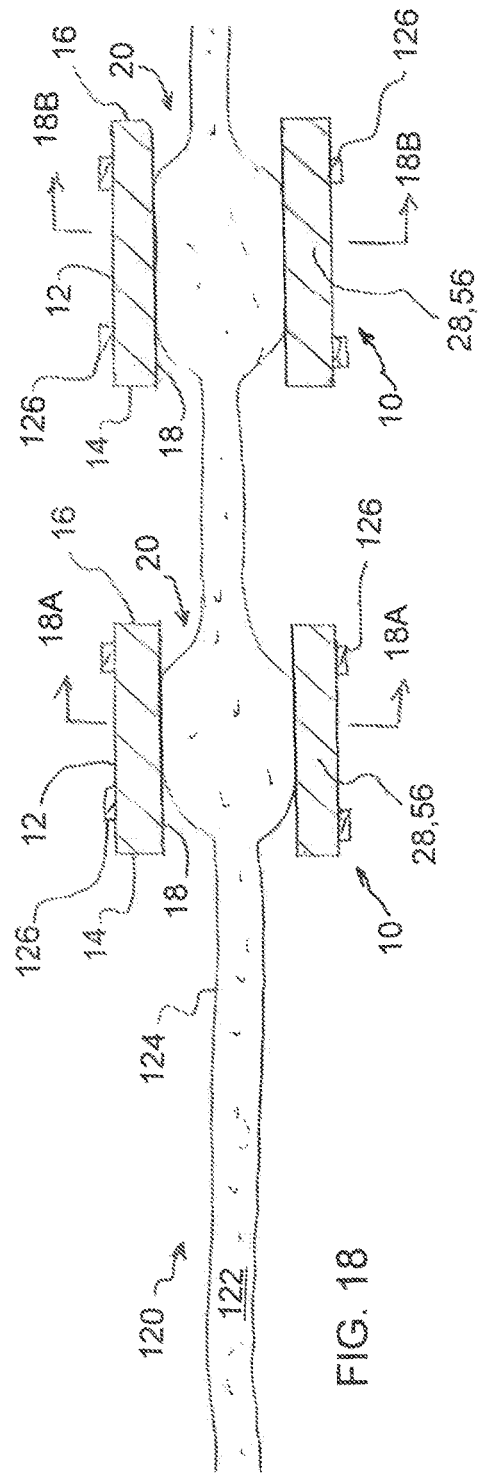
FIG. 18 is a diagrammatic cross sectional view of a portion of the artery with the thoracic/fusiform aortic aneurysm being wrapped and supported by the device according to the present invention and an abdominal/sacular aortic aneurysm being wrapped and supported by the device according to the present invention.
Figure 18A:
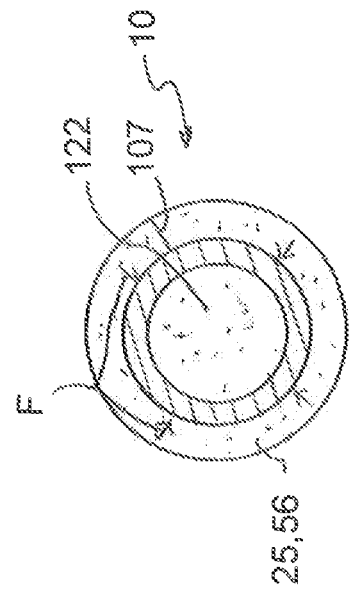
FIG. 18A is a sectional view, along section line 18A-18A of FIG. 18, of the thoracic/fusiform aortic aneurysm wrapped and supported by the device according to the present invention.
Figure 18B:
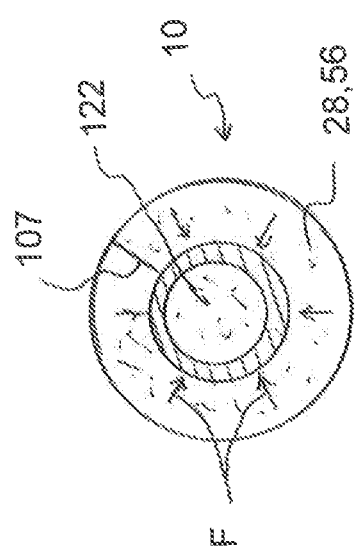
FIG. 18B is a sectional view, generally along section line 18B-18B of FIG. 18, of the abdominal/sacular aortic aneurysm wrapped and supported by the device according to the present invention.

As mentioned above, the shape and dimensions of the device 10 depend somewhat on the physiological functional need/requirement of the patient. For example, an axially length of the device 10, i.e., the length from the inlet surface 14 to the outlet surface 16, is generally in the range of between about 2 cm and about 15 cm, and more preferably in the range of between about 3 cm and about 9 cm. As shown in FIGS. 18, 18A and 18B, the device 10 is substantially cylindrical and the passage 20, in its uncompressed state, has an internal passage diameter of between about 1.5 mm and about 5 mm, more preferably between about 2 mm and about 4.5 mm while the device has an outer diameter which is preferably in the range of between about 3 cm and about 9 cm, and more preferably in the range of between about 4 cm and about 7 cm. The compressible pliant material has a thickness which is typically in the range of between about 0.75 cm and about 2.5 cm.

The matriculation process of a patient with the device 10 surgically implanted will now be described further. As generally shown, the artery 120 enters the device 10, via an inlet 22 defined by the first inlet end surface 14 of the device 10. The artery 120 extends along the passage 20, completely through the device 10, and eventually exits the device 10 via the outlet 24 formed in the outlet end surface 16.

The inner wall or surface 18 of the device 10, through which the artery 120 passes, is compliant, pliable or ductile such that the inner wall or surface 18 can respond to different forces and/or pressures exerted thereon, i.e., be compressed, and thereby prevent excessive or overexpansion of artery wall 124. That is, the inner wall or surface 18 of the device 10, in its generally uncompressed state, is normally slightly compressed toward the circumferential outer surface 12 of the device 10, or possibly slightly spaced from the outer wall of the artery 120, i.e., the generally uncompressed/slightly compressed state of the device 10. In this generally uncompressed state, the inner wall or surface 18 of the device 10 permits the normal flow of blood 122 through the artery 120 by exerting only slight or minimal constriction pressure on the outer wall of the artery 120, or possibly no constriction pressure. In the event that the blood pressure flowing through the weakened section of the artery 120 eventually increases for some reason, as the wall of the artery 120 attempts to expand radially and increase circumferentially in diameter, the outer surface of the artery wall 124 abuts against and attempts to expand into the inner wall or surface 18 of the device 10. As a result, in order for the artery wall 124 to continue to expand, the artery wall 124 must force the inner wall or surface 18 of the device 10 radially outwardly and compress the pliant material 28, 56, accommodated between the inner wall or surface 18 and the circumferential outer surface 12 of the device 10. Such compression of the wall or surface 18 as well as the pliant material 28, 56, accommodated between the inner wall or surface 18 and the circumferential outer surface 12 of the device 10, opposes further expansion of artery wall 124 and thereby provide support to the weakened outer wall of the artery 120 and minimizes expansion of the artery wall 124. As a result of such support, the increase in blood pressure within the artery is distributed to and along other areas or sections of the artery 120 thereby assisting with avoiding rupture of the weakened section of the artery 120 that is supported by the device 10.

As the inner wall or surface 18 and the pliant material 28, 56 are compressed by the weakened artery 120 wall attempting to expand, the inner wall or surface 18 and the compressed material device 10, in turn, exert an opposing force on the weakened wall of the artery 120 and this force is directed at collapsing or constricting the artery wall 124 back toward its initially expanded state in which blood 122 is still permitted to reliably and consistently flow along the artery 120 and be delivered to a remainder of the body.

In the generally normal uncompressed state of the device 10, only a minimal constriction pressure or force F, such as a constrictive or collapsing force (see FIGS. 18A and 18B), or possibly no force, is applied by the inner wall or surface 18 against the outer wall of the artery 120. That is, in the normal slightly compressed state of the device 10, the inner wall or surface 18 only applies a minor radially inward constriction pressure or force F against the outer surface of the artery 120, or possibly no force, so that the diameter of the passage 20 is biased toward its uncompressed diameter which normally permits the flow of blood 122 through the artery 120.

Figure 19A:
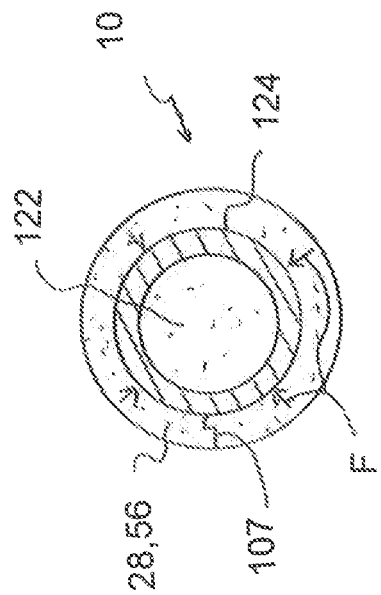
FIG. 19A is a sectional view, similar to FIG. 18A, diagrammatically showing the constrictive force generated by the device which opposed expansion of the thoracic/fusiform aortic aneurysm.
Figure 19B:
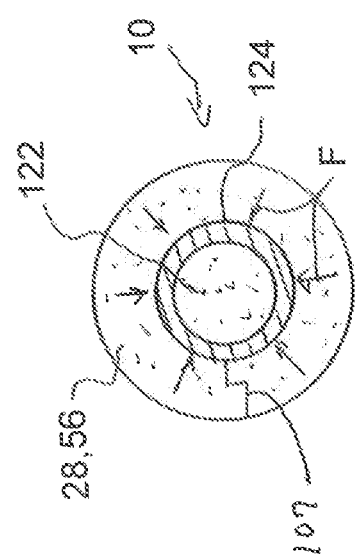
FIG. 19B is a sectional view, similar to FIG. 18B, diagrammatically showing the constrictive force generated by the device which opposed expansion of the abdominal/sacular aortic aneurysm.

In the compressed state of the device 10, as shown FIGS. 19A and 19B, the inner wall or surface 18 is sufficiently expanded in diameter/dimension so that the pliant material 28, 56 is, in turned, compressed and generates a constriction pressure or force F (such as a constrictive or collapsing force) which is applied on and/or by the inner wall or surface 18, generally in a radially inward direction, as indicated in both of these figures, so as to bias the internal dimensions of the passage 20 back toward its normal slightly compressed, or possibly uncompressed, state. Such constriction pressure or force F thereby biases the weakened wall of the artery 120 back toward a desired diameter or condition which still permits the flow of blood 122 through the artery 120 while avoiding rupture of the weakened section of the artery 120. That is, in the compressed state of the device 10, the inner wall or surface 18 applies the constriction pressure or force F directed radially inward toward and against the outer wall of the artery 120 so that the diameter of the passage 20 is biased back toward its initial generally uncompressed/ slightly compressed state or condition which permits the normal flow of blood 122 through the artery 120.

Figure 18C:
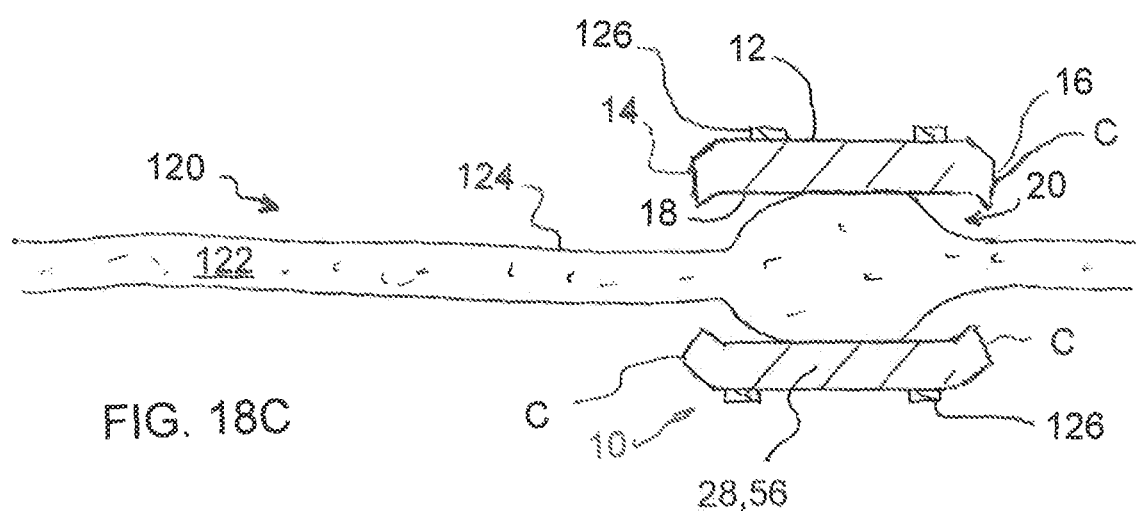
FIG. 18C is a sectional view, similar to FIG. 18, showing a vascular aneurysm wrapped and supported by a modification form of the device which includes a pair of opposed cuffs.

As generally shown in FIG. 18C, each opposed axial end of the device 10 may be provided with a respective cuff C which gradually tapers toward a smaller diameter area or region. Each one of the opposed cuffs C, of slightly smaller diameter, assists with containing the weakened section of the vascular aneurysm between the pair of cuffs C while still supporting the same and assists with holding the device in place or in the desired position or location.

As with the previous embodiments, preferably the device 10 has an elongate cut or slit 107 that extends from an outer wall radially inwardly toward the passage 20 and along the entire axial length of the device 10. During the surgical procedure, the slit 107 is separated so as to facilitate placing the device 10 completely around the desired section or sections of the artery 120 to be supported so that the desired section or sections of the artery 120 is/are completely surrounded and accommodated within the passage 20. This embodiment avoids having to cut or otherwise sever the artery 120 in order to install the device 10. As with the previous embodiments, one or more rib(s) or other circumferential element(s) can wrap or extend completely around the outer wall or surface of the device 10 to assist with maintaining the slit 107 in the substantially closed position. Alternatively or in addition, one or more locking clamps, ties, bands or other members 126 completely surround the outer circumference of the device 10 and thereby permanently maintain the slit 107 in a closed configuration, i.e., the one or more locking clamps, ties, bands or other members 126 prevent the mating surfaces, which define the slit 107, from inadvertent becoming separated from one another and thereby opening of the slit 107 following surgery. It is to be appreciated that the slit 107 could, if desired, be permanently sealed by ultrasonic welding or some other similar closure method or technique.

Figure 20:
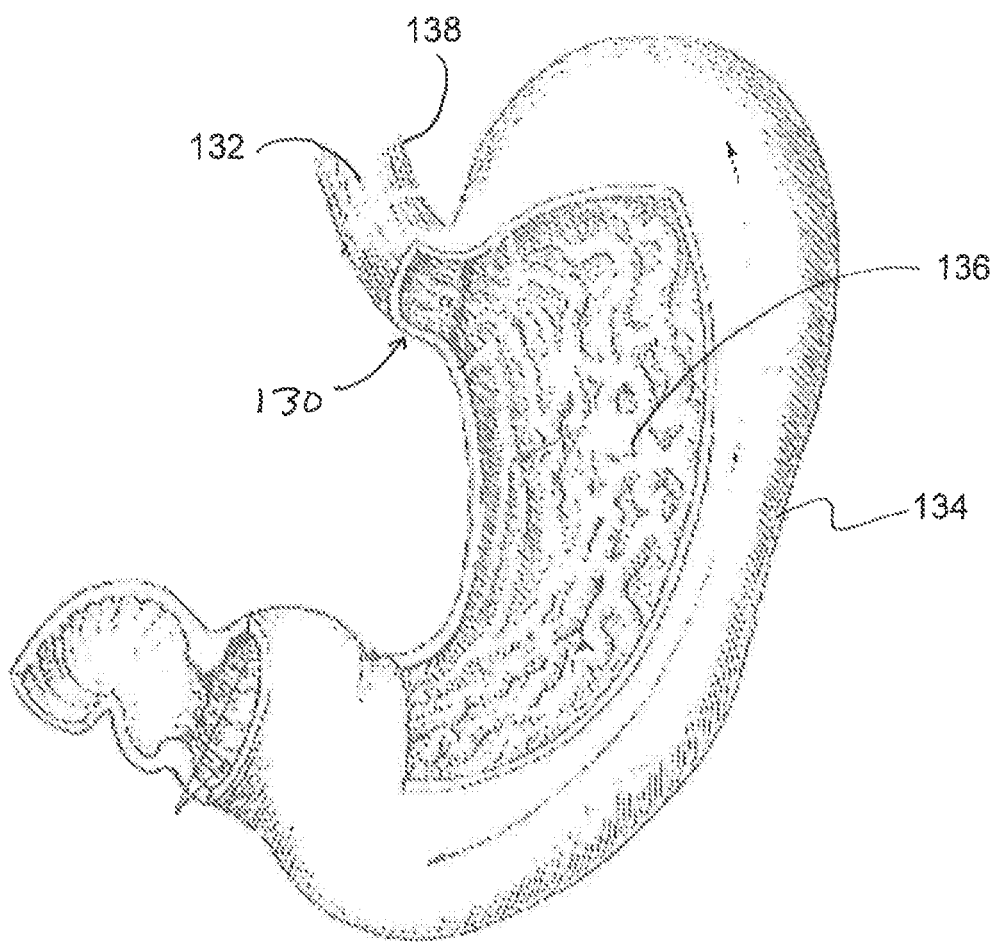
FIG. 20 is a diagrammatic cross sectional view of showing a typically esophageal sphincter communicating with a stomach which permits the flow of food and fluid into the stomach.

Turning now to FIGS. 20-21A, an additional embodiment of the present invention will now be described in detail. As this additional embodiment is quite similar to the embodiment of FIGS. 17-19B, similar or like elements are given the same reference numerals.

As with the immediately previous embodiment, the device 10 is designed to enclose, encase and/or completely wrap around the bodily organ and permit the bodily organ to function generally in its normal operating condition, e.g., permit limited expansion to permit material/fluid to flow therethrough, and as well as generate a contraction force, which opposes somewhat the expansion of the bodily organ and assists with returning the bodily organ back to its desired operational state in which the bodily organ inhibits from material/fluid from passing therethrough. Following installation by a surgical procedure, the device 10 completely surrounds the bodily organ and is arranged and designed to permit some radial expansion of the bodily organ but prevent excessive or over expansion of the bodily organ.

The bodily organ, diagrammatically shown in FIG. 20, is an esophageal sphincter 130 through which food, fluid and other consumables 132, which were eaten or swallowed, to enter into the stomach 134 for digestion. As is well known in the art, the esophageal sphincter 130 is a bundle of muscles which generally function as a one-way valve which normally and readily expands to allow the desired food, fluid and other consumables 132 to be digested to enter into the stomach 134 and lower intestines and, thereafter, normally constricts so as to prevent any partially digested material 136, located within the stomach 134 and commencing the digestion process, from flowing back into the esophagus 138 or the windpipe (not shown). In some individuals, over time, the bundle of muscles of the esophageal sphincter 130 gradually weaken and fail to function properly, e.g., the bundle of muscles of the esophageal sphincter 130 fail to sufficiently constrict and prevent the back flow of and partially digested material 136 from the stomach 134 back into the esophagus 138 and/or windpipe. This, in turn, leads to acid reflux or regurgitation and discomfort to the patient whose bundle of muscles of the esophageal sphincter 130 are not function properly and may possibly eventually result in a cancerous situation.

As is conventional, an outer diameter of a normal functioning esophageal sphincter 130 is typically between 1.5 cm and 3.5 cm but an outer diameter of the esophageal sphincter 130, during normal operation when permitting food, fluid and other consumables 132 to flow therethrough into the stomach 134, may possibly expand to between 2.0 cm and 5.0 cm or so, as exterior diameter of the esophageal sphincter 130 increases while the food, fluid and other consumables 132 to be digested pass therethrough and flow toward the stomach 134. In addition, the outer diameter of such esophageal sphincter 130, during normal operation once the food, fluid and other consumables 132 to be digested passes therethrough, typically decreases in size back toward a closed state which again prevents the back flow of any the partially digested material 136 from the stomach 134 back into the esophagus 138 and/or windpipe.

The present invention is directed at providing support circumferential around the weakened muscles of the esophageal sphincter and esphagus 130, and thereby provide circumferential and radial support for the weakened muscles of the esophageal sphincter 130. The device 10 is designed to assist with returning the esophageal sphincter 130 back to is normal state in which the weakened muscles of the esophageal sphincter 130 are sufficiently constricted so as to prevent the back flow of any partially digested material 136 from the stomach 134 into the esophagus 138 and/or windpipe while the device 10 is also designed so as to permit sufficient expansion of the muscles of the esophageal sphincter 130, but prevent excessive or overexpansion thereof, so that food, fluid and other consumables 132 to be digested can readily pass therethrough and flow toward the stomach 134.

As generally shown in FIG. 21, the device 10 is designed, e.g., size and shaped, so as to completely surround the weakened section of the weakened muscles of the esophageal sphincter 130 and provide circumferential support which assists with constricting the weakened muscles of the esophageal sphincter 130 back toward a state in which such muscles of the sphincter prevent the back flow of any partially digested material 136 from the stomach 134 into the esophagus 138 and/or windpipe. Typically, as shown, the device 10 has an axial length that may be as long or possibly longer than the axial length of the weakened section of the weakened muscles of the esophageal sphincter 130 so that the device 10 may partially overlap, on both opposed axial ends thereof, non-weakened, normal functioning sections of the muscles of the esophageal sphincter 130. It is to be appreciated that the extent, if any, of the overlap of the non-weakened, normal functioning sections of the esophageal sphincter 130 on each opposed end of the device 10 can vary from application to application, e.g., between 0.2 cm and about 0.5 cm, for example.

As with the previous embodiment, the device 10 has a central passage 20 that extends completely axially through the device 10, from the inlet end surface 14 to and the outlet end surface 16. A radially inner surface 18 of the device 10 defines the passage 20 and this radially inner surface 18 of the passage 20 is designed, during use, to directly engage with the outer wall of the esophageal sphincter 130 and thereby sightly bias, constrict and/or force the outer wall of the muscles of the esophageal sphincter 130 radially inwardly so as to slightly decrease the diameter of the esophageal sphincter 130 and prevent the back flow of any partially digested material 136 from the stomach 134 into the esophagus 138 and/or windpipe, but without significantly obstructing the passage of food, fluid and other consumables 132 to be digested into the stomach 134.

That is, the weakened muscles of the esophageal sphincter 130 are normally accommodated within the passage 20 and surrounded by the inner surface so that the device 10 completely surrounds and supports the weakened section of the esophageal sphincter 130. It is important to note that according to this embodiment, which is different from the previous embodiments, the radially inner surface 18 of the passage 20 is not designed to constrict or prevent the flow of food, fluid and other consumables 132 to be digested through the esophageal sphincter 130 and digested into the stomach 134. To the contrary, the device 10 wraps around and completely surrounds the esophagus/esophageal sphincter 130 and is designed to prevent excessive and/or overexpansion of the esophageal sphincter 130 to thereby assist with returning the esophageal sphincter 130 back to its back flow preventing condition.

As the muscles of the esophageal sphincter 130 attempt to expand, i.e., attempts to increase in diameter, to permit food, fluid and other consumables 132 to be digested to pass therethrough into the stomach 134, the outer wall of the esophageal sphincter 130 must also force the radially inner surface 18 of the passage 20 radially outwardly and thereby compress the pliant material 28, 56, located between the inner surface 18 and the outer surface 12 of the device 10. Such compression of the pliant material 28, 56, in turn, provides some resistance to further expansion of the esophagus/esophageal sphincter wall 140. The device 10 is designed to permit sufficient expansion of the bundle of muscles of the esophageal sphincter 130 so that the that food, fluid and other consumables 132 to be digested can pass therethrough and flow toward the stomach 134, but prevent excessive or over expansion of the bundle of muscles of the esophageal sphincter 130 so that, once food, fluid and other consumables 132 to be digested pass therethrough, of the muscles of the esophageal sphincter 130 can sufficiently constrict and prevent the back flow of and partially digested material 136 from the stomach 134 into the esophagus 138 and/or windpipe.

As mentioned above, the shape and dimensions of the device 10 depend somewhat on the physiological functional need/requirement of the patient. For example, an axially length of the device 10, i.e., the length from the inlet surface 14 to the outlet surface 16, for this embodiment is generally in the range of between about 1.5 cm and about 7.0 cm or so, and more preferably in the range of between about 2.0 cm and about 4.0 cm. As shown in FIGS. 21 and 21A, the device 10 is substantially cylindrical in shape and the passage 20, in its uncompressed state, has an internal passage diameter of typically between about 0.5 cm and about 0.7 cm, while the device 10 has an outer diameter which is preferably in the range of between about 2.0 cm and about 8.0 cm. The compressible pliant material has a thickness, which is in the range of between about 0.75 cm and about 3.65 cm.

The matriculation process of a patient with the device 10 surgically implanted will now be described further. As generally shown, a first section of the esophagus/esophageal sphincter 130 enters the device 10, via an inlet 22 defined by the first inlet end surface 14 of the device 10. The esophageal sphincter 130 extends along the passage 20, completely through the device 10, and eventually exits the device 10 via the outlet 24 formed in the outlet end surface 16 adjacent the stomach 134.

The inner wall or surface 18 of the device 10, through which the esophageal sphincter 130 passes, is compliant, pliable or ductile such that the inner wall or surface 18 can respond to different forces and/or pressures exerted thereon, i.e., be compressed, and thereby support the esophageal sphincter 130 and prevent the excessive or overexpansion of the esophageal sphincter 130. That is, the inner wall or surface 18 of the device 10, in its generally uncompressed state, is slightly compressed toward the circumferential outer surface 12 of the device 10 or possibly may be slightly spaced from the outer wall of the esophageal sphincter 130, i.e., the generally uncompressed/slightly compressed state of the device 10. In this generally slightly compressed state, the inner wall or surface 18 of the device 10 exerts only a slight or minimal constriction force or pressure on the outer wall of the esophageal sphincter 130 which prevents the back flow of any partially digested material 136 from the stomach 134 into the esophagus 138 and/or windpipe. When food, fluid and other consumables 132 to be digested attempt to pass or flow through the weakened muscles of the esophageal sphincter 130, the outer wall of the esophageal sphincter 130 attempts to expand radially and thereby increase circumferentially in diameter against a force supplied by the inner wall or surface 18. As a result, in order for the esophageal sphincter wall 140 to expand, the esophageal sphincter wall 140 must force the inner wall or surface 18 of the device 10 radially outwardly and compress the pliant material 28, 56, accommodated between the inner wall or surface 18 and the circumferential outer surface 12 of the device 10. Such compression of the wall or surface 18 as well as the pliant material 28, 56 accommodated between the inner wall or surface 18 and the circumferential outer surface 12 of the device 10, opposes expansion of esophageal sphincter wall 140 and thereby provides support to the weakened muscles of the esophageal sphincter 130 and minimize the expansion of the esophageal sphincter wall 140. As a result of such support, the food, fluid and other consumables 132 to be digested can pass therethrough and flow toward the stomach 134 while the muscles of the esophageal sphincter 130 are prevented from excessive or overexpansion and thereby eventually constrict back to its flow preventing size to prevent the back flow of any partially digested material 136 from the stomach 134 back into the esophagus 138 and/or windpipe.

As the inner wall or surface 18 and the pliant material 28, 56 are compressed by the weakened muscles of the esophageal sphincter 130 expanding, the inner wall or surface 18 and the compressed material device 10, in turn, exerts an opposing force on the weakened muscles of the esophageal sphincter 130 and this force F is directed at eventually collapsing or constricting the weakened outer wall of the esophageal sphincter 130 radially inward back toward its initially expanded state in which food, fluid and other consumables 132 to be digested are reliably and consistently prevented from flowing out of the stomach 134 into the esophagus 138 and/or windpipe.

In this generally uncompressed/slightly compressed state of the device 10, the inner wall or surface 18 of the device only exerts a minimal constriction pressure or force F, or possibly no constrictive or collapsing force, against the outer surface of the esophageal sphincter 130. That is, the inner wall or surface 18 only applies a minor radially inward directed constriction pressure or force F against the outer surface of the esophagus/esophageal sphincter 130, or possibly no force, so that the diameter of the passage 20 is biased toward a diameter which prevents back flow of and partially digested material 6 from the stomach 134 into the esophagus 138 and/or windpipe.

In the compressed state of the device 10, as shown FIG. 22, the inner wall or surface 18 is sufficiently expanded in diameter/dimension and the pliant material 28, 56 is sufficiently compressed so that the pliant material 28, 56 generates an opposing generally radially inward directed constriction pressure or force F (such as a constrictive or collapsing force), as indicated in this figure, which is transferred to the inner wall or surface 18 and tends to bias the internal dimensions of the passage 20 back toward its normal slightly compressed (or possibly uncompressed) state. Such constriction pressure or force F thereby biases the weakened muscles of the esophageal sphincter 130 back toward its normal state or condition which prevents the back flow of any partially digested material 136 from the stomach 134 into the esophagus 138 and/or windpipe. That is, in the compressed state of the device 10, the inner wall or surface 18 applies the constriction pressure or force F radially inward toward and against the outer wall of the esophageal sphincter 130 so that the diameter of the passage 20 is biased back toward its initial unbiased state or condition which prevents the back flow of any partially digested material 136 from the stomach 134 into the esophagus 138 and/or windpipe.

As with the previous embodiments, preferably the device 10 has an elongate cut or slit 107 that extends from an outer wall radially inwardly toward the passage 20 and along the entire axial length of the device 10. During the surgical procedure, the slit 107 is separated so as to facilitate placing the device 10 completely around the desired section of the esophagus/esophageal sphincter 130 to be supported so that the desired section of the esophageal sphincter 130 is completely surrounded and accommodated within the passage 20. This embodiment avoids having to cut or otherwise sever the esophagus or esophageal sphincter 130 in order to install the device 10.

As with the previous embodiments, one or more rib(s) or other circumferential element(s) can wrap or extend completely around the outer wall or surface of the device 10 to assist with maintaining the slit 107 in the substantially closed position. Alternatively or in addition, one or more locking clamps, ties, bands or other members 126 completely surround the outer circumference of the device 10 and thereby permanently maintain the slit 107 in a closed configuration, i.e., the one or more locking clamps, ties, bands or other members 126 prevent the mating surfaces, which define the slit 107, from inadvertent becoming separated from one another and thereby opening of the slit 107 following surgery. It is to be appreciated that the slit 107 could, if desired, be permanently sealed by ultrasonic welding or some other similar closure method or technique.

It will be appreciated did that the axial length of the device 10 may vary from application to application. That is, the device 10 may be axially long enough to generally abut against the stomach 134, adjacent one axial end thereof and not only completely encompass and surround the esophageal sphincter 130, but also completely encompass and surround a portion of the esophagus 138, e.g., any herniated portion of the esophagus 138, located remotely from the stomach 134 technique.

Although not shown, each opposed axial end of the device 10 may be provided with a cuff C which gradually tapers toward a smaller diameter region. Each one of the opposed cuffs C, of slightly smaller diameter, assists with containing the weakened section of the esophageal sphincter 130 between the pair of cuffs C while still supporting the same.

Figure 23:
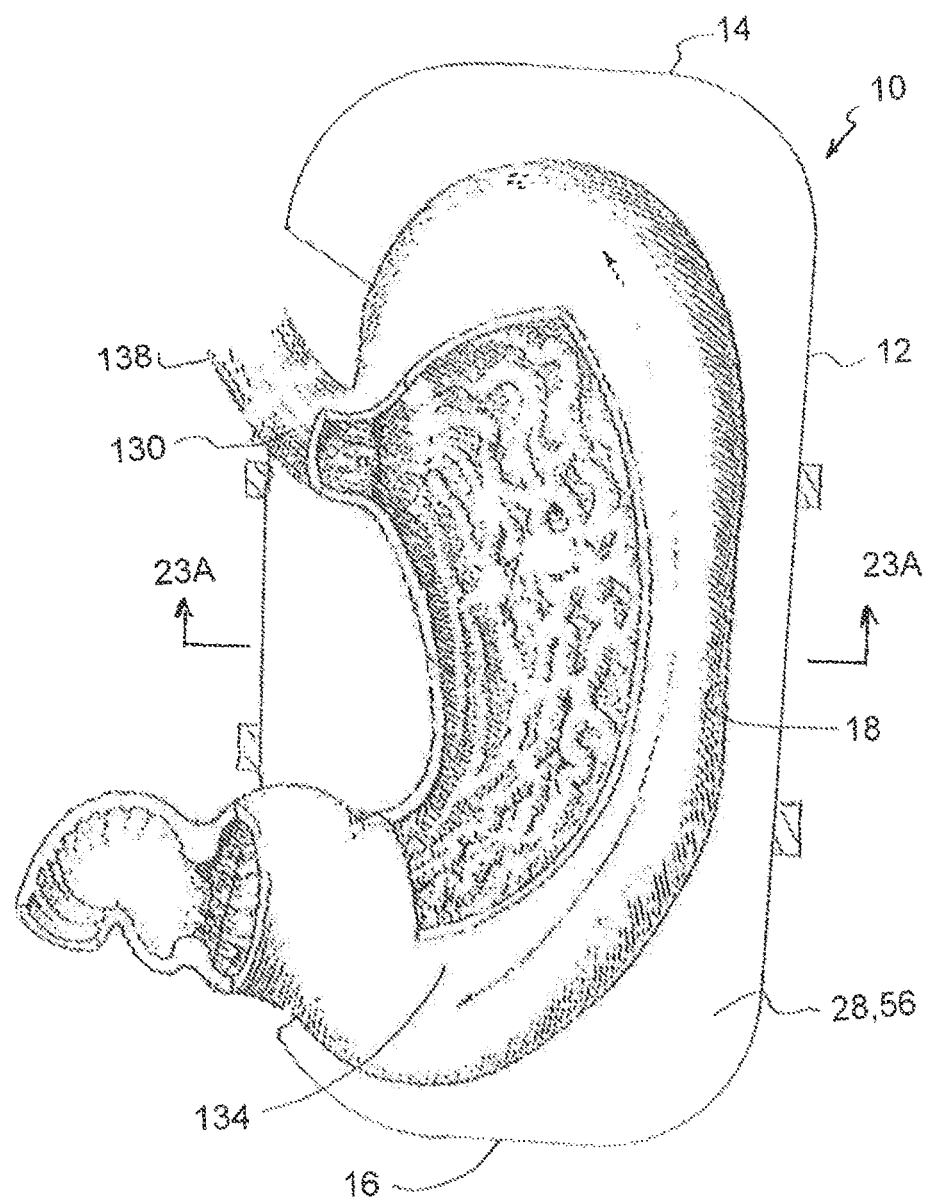
FIG. 23 is a diagrammatic cross sectional view showing the stomach being wrapped and supported by the device according to the present invention.
Figure 24:
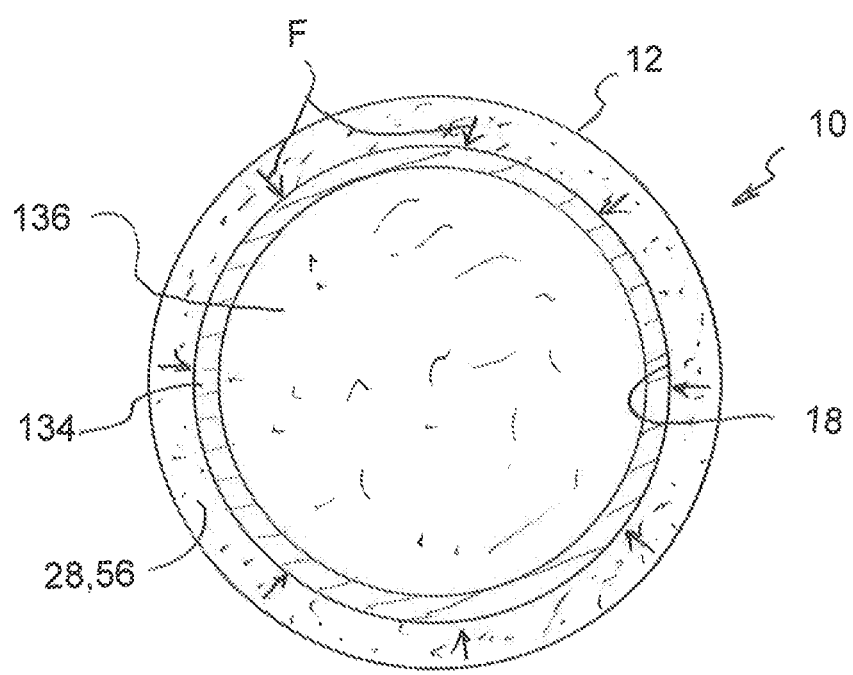
FIG. 24 is a diagrammatic cross-sectional view, similar to section line 23A-23A of FIG. 23, diagrammatically showing the constrictive force generated by the device which opposed expansion of the stomach.

Turning now to FIGS. 23-24, an additional embodiment of the present invention will now be described in detail. As this additional embodiment is quite similar to the embodiment of FIGS. 17-22, similar or like elements are given the same reference numerals.

As with the immediately previous two embodiments, the device 10 is designed to enclose, encase and/or completely wrap around the bodily organ and permit the bodily organ to function generally in its normal operating condition, e.g., permit material/fluid to passing therethrough and also permit limited expansion and as well as generate a contraction force, which opposes somewhat the limited expansion of the bodily organ to assists with returning the bodily organ back to its desired operational state. Following installation by a surgical procedure, the device 10 completely surrounds the bodily organ and is arranged and designed to permit some radial expansion of the bodily organ but prevent excessive or over expansion of the bodily organ.

The bodily organ, diagrammatically shown in FIG. 23-24, is a stomach 134 of an individual into which food, fluid and other consumables 132, which are eaten or swallowed, enter into commence the conventional digestion process. As is well known in the art, the stomach 134 is a muscular organ located on the left side of the upper abdomen. The stomach 134 receives food, fluid and other consumables 132 from the esophagus 138 and secretes acid and enzymes that assist with digesting the food, fluid and other consumables 132. The stomach 134 muscles periodically contract thereby churning the food, fluid and other consumables 132 so as to enhance the digestion process. A typical stomach 134 of an adult human being, in an empty state, has a volumetric capacity of about 0.25 liters or so while the typical stomach 134, when substantially completely filled with food, fluid and/or other consumables 132, can expand to a volume of about 1 liter or so. The stomach 134 normally expands to accommodate consumed food, fluid and other consumables 132 and thereafter gradually shrinks or contracts, back to its normal substantially empty state, as the consumed food, fluid and other consumables 132 are partially digested and eventually transferred to the small and the large intestines.

As is well known in the art, there are a number of procedures with assist with limiting the extent to which the stomach is permitted to expand when an individual is consuming food, fluid and/or other consumables 132. However, most of these commonly known procedures involve seriously impact the overall functionality of the stomach 134 and thus are not desirable.

As is conventional, an outer diameter of a normal functioning empty stomach 134 is typically between 12 and 17 cm but an outer diameter of the stomach 134, during normal operation when digesting food, fluid and other consumables 132, may possibly expand to a diameter of between 17 cm and 26 cm, while the axial length of a normal functioning empty stomach 134 is typically between 25 cm and 31 cm but the axial length of the stomach 134, during normal operation when digesting food, fluid and other consumables 132, may possibly expand to a length of between 27 cm and 40 cm. After consuming and commencing digestion of the food, fluid and other consumables 132, the outer diameter and/or axial length of the stomach 134, during normal operation while digesting the food, fluid and other consumables 132, typically gradually decreases in size and length back to a diameter of approximately 13 cm and 16 cm, respectively.

The present invention is directed at providing support circumferential around circumference of the stomach 134 and preferably also limiting axial lengthening of the stomach 134, and thereby provide circumferential, radial and axial support for the stomach 134 so as to prevent excessive or overexpansion of the stomach 134. The device 10 is designed to assist with permitting limited expansion of the stomach 134 to allow digestion of an adequate quantity of food, fluid and other consumables 132, but preventing excessive or over expansion thereof, so as to limit the amount of food, fluid and other consumables 132 that can be accommodated within the stomach 134, at any given time. Such limited expansion of the stomach 134, due to the resistance provided by the device 10, provides a sensation to the individual so that the individual generally feels "full," after eating a smaller, limited quantity of food, fluid and other consumables 132, and thus is more prone to discontinue eating, drinking and/or consuming food, fluid and other consumables 132 at an earlier point in time. According to the present invention, the stomach 134 functions and digests food, fluid and other consumables 132 in its normal fashion. However, since there is less food, fluid and other consumables 132 in the stomach 134, the stomach tends to transfer the food, fluid and other consumables 132 more quickly to the small intestine for further digestion and the stomach 134, in turn, gradually returns back to is normal empty state. As this stomach is prevented from overexpanding, the stomach 134 processes less food, fluid and other consumables 132 and this can assist with controlling the appetite of the individual.

Figure 23A:
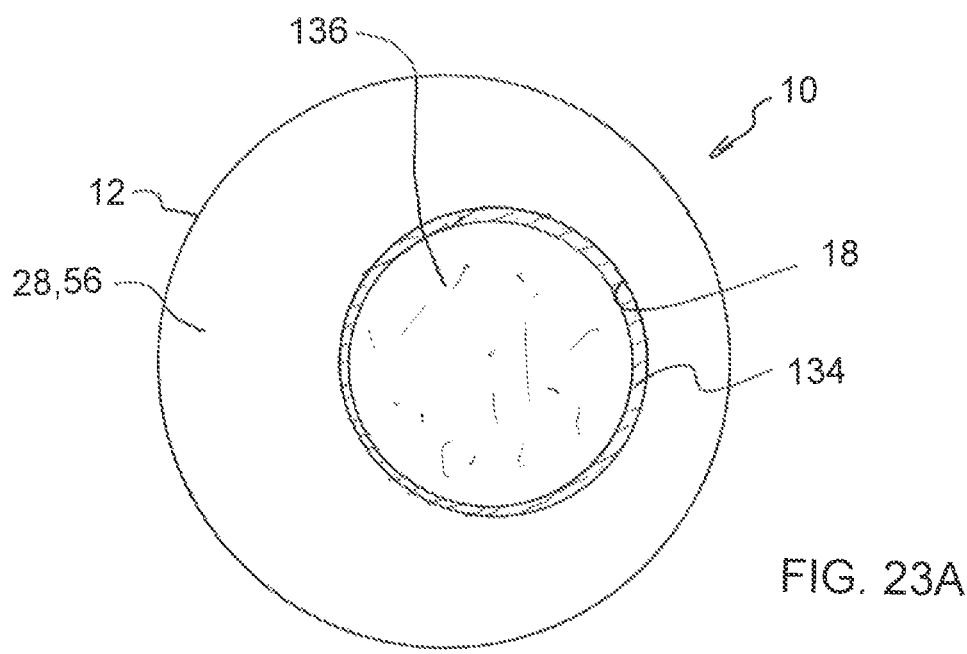
FIG. 23A is a diagrammatic cross-sectional view, along section line 23A-23A of FIG. 23, diagrammatically showing the slight or minimum constrictive force initially generated by the device which biases the stomach into its minimum volume condition.

As generally shown in FIGS. 23 and 23A, the device 10 is designed, e.g., size and shaped, so as to completely surround the stomach muscles and provide circumferential support, from the stomach entrance at the level of the esophagal sphincter to the end at the level the pyloric sphincter, which assists with providing a constriction force to the outer surface of the muscles of the stomach 134 and force them back toward a generally empty state in which the stomach 134 accommodates a minimum volume of food, fluid and other consumables 132. Typically, as shown, the device 10 has an axial length that is as long or possibly slightly longer than the axial length of the stomach 134. The device 10 is preferably slightly longer than the axial length of the stomach 134 and may be decrease in dimension or diameter, at each opposed end of the device 10 so that the device assist with limiting axial expansion of the stomach 134 as the stomach muscles stretch while consuming food, fluid and other consumables 132.

As with the previous embodiment, the device 10 has a central passage 20 that extends completely axially through the device 10, from the inlet end surface 14 to and the outlet end surface 16. A radially inner surface 18 of the device 10 defines the passage 20 and this radially inner surface 18 of the passage 20 is designed, during use, to directly engage with the outer wall of the stomach 134 and thereby sightly bias, constrict and/or force the outer wall 142 of the stomach 134 radially inwardly so as to slightly decrease the diameter of the stomach 134 back to its minimum dimension/volume, but without significantly obstructing the passage of food, fluid and other consumables 132 to be digested into and out of the stomach 134.

That is, the stomach 134 is accommodated within the passage 20 and completely surrounded by the inner surface 18 so that the device 10 completely surrounds and supports the stomach 134. It is important to note that according to the invention, the radially inner surface 18 of the passage 20 is not designed to prevent the flow of food, fluid and other consumables 132 to be digested into the stomach 134 and commencing the digestive process. To the contrary, the device 10 wraps around and completely surrounds the stomach 134 and is designed to prevent excessive and/or overexpansion of the stomach 134 from its entrance to its exit to thereby assist with limiting the quantity of food, fluid and other consumables 132 which can be accommodated within the stomach 134 and returning the stomach 134 back to its substantially empty or minimum volume/capacity.

As the stomach muscles attempt to expand, i.e., attempt to increase in diameter or size, as food, fluid and other consumables 132 enter into and are accommodated within the stomach 134 to commence the digestion process, the outer wall 142 of the stomach 134 muscles began to stretch and force the inner surface 18 of the passage 20 radially outwardly and thereby compress the pliant material 28, 56, located between the inner surface 18 and the outer surface 12 of the device 10. Such compression of the pliant material 28, 56, in turn, provides some resistance to further expansion of the stomach wall 142. The device 10 is designed to permit sufficient limited expansion of the stomach muscles so that the that food, fluid and other consumables 132 to be digested can continue to enter and flow into the stomach 134, but the device 10 is designed to limit the amount/quantity of food, fluid and other consumables 132 which can be accommodated within the stomach 134 for digestion and thereby prevent excessive or overexpansion of the stomach muscles.

As mentioned above, the shape and dimensions of the device 10 depends somewhat on the physiological functional need/requirement of the patient. For example, an axially length of the device 10, i.e., the length from the inlet surface 14 to the outlet surface 16, is generally in the range of between about 34 cm and about 45 cm, and more preferably in the range of between about 32 cm and about 38 cm. As shown in FIG. 23, the device 10 is substantially cylindrical and the passage 20, in its uncompressed state, has an internal passage diameter of between about 12 and 17 cm while the device 10 and has an outer diameter which is preferably in the range of between about 19 cm and 30 cm. The compressible pliant material has a thickness, in its uncompressed state, which is in the range of between about 4.5 cm and 12 cm.

The matriculation process of a patient with the device 10 surgically implanted will now be described further. As generally shown, the stomach 134 is completely surrounded by the device 10. That is, the stomach 134 extends along the passage 20, completely through the device 10, and so that the esophageal sphincter enters through the inlet 22 formed in the inlet end surface 14 of the device 10 while the pyloric sphincter exits through the outlet 24 formed in the outlet end surface 16. In some applications, it may be desirable for the device 10 to at least partially close off both axial ends of the device 10 so as to limit axial expansion of the stomach 134 when consuming food, fluid and other consumables 132.

The inner wall or surface 18 of the device 10, through which the stomach 134 passes, is compliant, pliable or ductile such that the inner wall or surface 18 can respond to different forces and/or pressures exerted thereon, i.e., be compressed, and thereby support and/or reinforce the muscles of the stomach 134 and prevent the excessive or overexpansion of the stomach 134. That is, the inner wall or surface 18 of the device 10, in its generally uncompressed/slightly compressed state of the device 10, is either slightly spaced from the outer wall 142 of the stomach 134 or is slightly compressed by the stomach wall 142 toward the circumferential outer surface 12 of the device 10. In this generally uncompressed/slightly compressed state of the device 10, i.e., the inner wall or surface 18 of the device 10 either exerts no force or only exerts a slight or minimal constriction force against the outer wall 142 of the stomach 134 which tends to bias the stomach 134 back toward its minimum volume/capacity.

When food, fluid and other consumables 132 to be digested enter into the stomach 134, the outer wall 142 of the stomach 134 attempts to expand radially and increase circumferentially in diameter/volume against the force provided by the inner wall or surface 18. As a result, in order for the stomach wall 142 to expand, the stomach wall 142 must also force the inner wall or surface 18 of the device 10 radially outwardly and compress the pliant material 28, 56, accommodated between the inner wall or surface 18 and the circumferential outer surface 12 of the device 10. Such compression of the wall or surface 18 as well as the pliant material 28, 56 accommodated between the inner wall or surface 18 and the circumferential outer surface 12 of the device 10, opposes further expansion of stomach wall 142 and thereby provides support and resistance to further expansion of the stomach 134 which limits and/or minimize the expansion of the stomach wall 142. As a result of such support and resistance, the amount or quantity of food, fluid and other consumables 132 that can flow into and be accommodate by the stomach 134 is limited or restricted and this, in turn, tends to decrease the amount of food, fluid and other consumables 132 which are consumed by the individual.

As the inner wall or surface 18 and the pliant material 28, 56 are compressed by the expansion of the stomach 134, the inner wall or surface 18 and the compressed material device 10, in turn, exerts an opposing force on the stomach 134 and this force F is directed at eventually collapsing or constricting the stomach 134 back toward its empty state or minimum dimension/volume.

When the device 10 is generally in the uncompressed state or possibly slightly compressed state, i.e., the generally uncompressed/slightly compressed state of the device 10, only a minimal constriction pressure or force F, or possibly no constrictive or collapsing force F, is applied by the inner wall or surface 18 against the outer wall 142 of the stomach 134. That is, the inner wall or surface 18 only applies a minor radially inward constriction pressure or force F against the outer surface of the stomach 134, or possibly no force at all, so that the diameter of the passage 20 is biased toward its empty state and minimum volume/capacity.

In the compressed state of the device 10, as shown FIG. 24, the inner wall or surface 18 is sufficiently expanded in diameter/dimension and the pliant material 28, 56 compressed so that the pliant material 28, 56 generates a constriction pressure or force F (such as a constrictive or collapsing force) which is applied on and/or by the inner wall or surface 18, generally in a radially inward direction as indicated, directed at biasing the internal surface of the passage 20 back toward its generally uncompressed/slightly compressed state. Such constriction pressure or force F thereby also biases the stomach 134 back toward its minimum volume/capacity. That is, in the compressed state of the device 10, the inner wall or surface 18 applies the constriction pressure or force F radially inward toward and against the outer wall 142 of the stomach 134 so that the diameter of the passage 20 is biased back toward its initial empty state or condition which the stomach 134 is in its minimum dimension/volume.

As with the previous embodiments, preferably the device 10 has an elongate cut or slit 107 that extends from an outer wall radially inwardly toward the passage 20 and along the entire axial length of the device 10. During the surgical procedure, the slit 107 is separated so as to facilitate placing the device 10 completely around the stomach 134 to be supported so that the stomach 134 is completely surrounded and accommodated within the passage 20. This embodiment avoids having to cut or otherwise sever the stomach 134 in order to install the device 10. As with the previous embodiments, one or more rib(s) or other circumferential element(s) can wrap or extend completely around the outer wall or surface of the device 10 to assist with maintaining the slit 107 in the substantially closed position. Alternatively or in addition, one or more locking clamps, ties, bands or other members 126 completely surround the outer circumference of the device 10 and thereby permanently maintain the slit 107 in a closed configuration, i.e., the one or more clamps, ties, bands or other members 126 prevent the mating surfaces, which define the slit 107, from inadvertent becoming separated from one another and thereby opening of the slit 107 following surgery. It is to be appreciated that the slit 107 could, if desired, be permanently sealed by ultrasonic welding or some other similar closure method or technique.

Although not shown, each opposed axial end of the device 10 may be provided with a cuff C which gradually tapers toward a smaller diameter region. Each one of the opposed cuffs C, of slightly smaller diameter, assists with containing the weakened section of the stomach 134 between the pair of cuffs C while still supporting the same.

It is to be appreciated that the cut or slit 107 can have virtually any desired shape or configuration as long as the cut or slit 107 permits separation of the device 10, along its longitudinal length, to facilitate wrapping the device 10 completely around the bodily organ to be supported.

Since certain changes may be made in the above described device for the treatment of urinary incontinence, without departing from the spirit and scope of the invention herein involved, it is intended that all of the subject matter of the above description or shown in the accompanying drawings shall be interpreted merely as examples illustrating the inventive concept herein and shall not be construed as limiting the invention.

I claim:

1. A device that is configured to wrap around a stomach of a patient and preventing overexpansion thereof in a radial direction as well as limiting axial lengthening thereof in an axial direction, the device comprising;

a body comprising an inner surface and an outer surface, and a compressible pliant material being located between the inner surface and the outer surface of the body;

the inner surface of the body defining a passage that is adapted to accommodate the stomach of the patient, and the passage extending through the device from an inlet to an outlet of the device and having opposed first and second end surfaces;

the stomach, following surgical implantation of the device, is configured to be accommodated within the passage of the device and is configured to be completely circumferentially wrapped and surrounded by the device both in the radial direction as well as in the axial direction, between the opposed first and second end surfaces, such that an esophagus of the patient is configured to pass through the inlet of the device while a small intestine of the patient is configured to pass through the outlet of the device;

the inner surface of the device, in an uncompressed/ slightly compressed state of the device, defining a normal state due which is configured to provide circumferential support to an outer wall of the stomach and prevent overexpansion thereof in both the radial and axial directions while continuously permitting flow of bodily material into and through the stomach;

as the stomach attempts to expand radially from the normal state due to the bodily material flowing into and through the bodily organ stomach, the stomach is configured to abut against the inner surface of the device and the stomach is configured to radially bias the inner surface of the device radially outwardly into the compressible pliant material thereby compressing the compressible pliant material toward the outer surface of the device, and such compression of the inner surface and the compressible pliant material, as the outer wall of the stomach attempts to expand, correspondingly exerting a resisting force, against the outer wall of the stomach, which limits and opposes the expansion of the stomach and forces the outer wall of the stomach back toward and into its normal state of the outer wall of the stomach which permits the flow of the bodily material into and through the stomach; and as the stomach attempts to expand axially from the normal state due to the bodily material flowing into and through the stomach, the stomach is configured to abut against an inner surface of opposed first and second end walls of the device and the stomach is configured to axially bias the inner surfaces of the opposed first and second end walls of the device axially outwardly into the compressible pliant material thereby compressing the compressible pliant material toward the outer surface of the device, and such compression of the inner surface and the compressible pliant material, as the outer wall of the stomach attempts to expand axially, correspondingly exerting a resisting force against the outer wall of the stomach, which limits and opposes the expansion of the stomach in the axial direction and forces the outer wall of the stomach back toward and into its normal state of the outer wall of the stomach which permits the flow of the bodily material into and through the stomach.

2. The device for wrapping around the stomach and preventing overexpansion thereof according to claim 1, wherein the compressible pliant material comprises one of a foam, a gel, a liquid, or a gas, and the compressible pliant material is captively retained by the inner surface, the outer surface, the first and second end surfaces of the device; and the inner surface has a greater elasticity than an elasticity of the outer surface of the device.

3. The device for wrapping around the stomach and preventing overexpansion thereof according to claim 1, wherein the device has an elongate cut or slit that extends from the outer surface of the device to the passage and along an entire axial length of the device so that the elongate cut or slit, during a surgical implantation procedure, can be separated and facilitate placing the device completely around the stomach to be reinforced without having to sever the stomach in order to install the device.

4. The device for wrapping around the stomach and preventing overexpansion thereof according to claim 3, wherein at least one circumferential element wraps around the outer surface of the device and assists with maintaining the cut or slit in an initially implanted closed configuration to prevent mating surfaces of the cut or slit from inadvertently becoming separated from one another.

5. The device for wrapping around the stomach and preventing overexpansion thereof according to claim 3, wherein at least one locking clamp, tie, band or other circumferential member completely surrounds an outer circumference of the device and permanently maintains the cut or slit in an initially implanted closed configuration to prevent mating surfaces of the cut or slit from inadvertently becoming separated from one another.

6. The device for wrapping around the stomach and preventing overexpansion thereof according to claim 3, wherein at least one locking member permanently maintains the cut or slit in an initially implanted closed configuration to prevent mating surfaces of the cut or slit from inadvertently becoming separated from one another.

7. The device for wrapping around the stomach and preventing overexpansion thereof according to claim 1, wherein the device is adapted to wrap around, support and reinforce weakened muscles of an esophagus/esophageal sphincter of the stomach and is designed to prevent overexpansion thereof so that the weakened muscles or an area of herniation of the esophagus/esophageal sphincter can again return back to a normally sealed state, once the bodily material flows into and therethrough, and prevent back flow of any partially digested material or content from the stomach into the esophagus/esophageal sphincter.

8. The device for wrapping around the stomach and preventing overexpansion thereof according to claim 7, wherein the device has an axial length that is adapted to partially overlap non-weakened sections of the esophagus/esophageal sphincter by a distance of between 0.2 cm and 0.5 cm, and the non-weakened sections of the esophagus/esophageal sphincter being located at axially opposite ends of the weakened muscles of the esophagus/esophageal sphincter.

9. The device for wrapping around the stomach and preventing overexpansion thereof according to claim 7, wherein the inner surface of the device is adapted to expand such that, as the bodily material flows through the esophagus and the esophageal sphincter, the weakened muscles of the esophagus/esophageal sphincter expand in diameter and force the inner surface of the device radially outwardly and thereby compresses the pliant material, located between the inner surface and the outer surface of the device, and the compressed pliant material provides resistance to further expansion of the weakened muscles of the esophagus/esophageal sphincter, while still permitting the bodily material to flow through the esophageal sphincter, and, once the bodily material passes through the esophageal sphincter, the compressed pliant material and the inner surface assists with forcing the weakened muscles of the esophageal sphincter back into the normally sealed state or a closed state.

10. The device for wrapping around the stomach and preventing overexpansion thereof according to claim 7, wherein the device has an axial length, from the first end surface to the second end surface between 1.5 cm and 7.0 cm, the passage, in an uncompressed state, has an internal passage diameter of between 0.5 cm and 0.7 cm to facilitate the flow of the bodily material in the uncompressed state, the outer surface of the device has an outer diameter which is in the range of between 2.0 cm and 8.0 cm, and the compressible pliant material has a thickness which is in a range of between 0.75 cm and 3.65 cm.

11. The device for wrapping around the stomach and preventing overexpansion thereof according to claim 1, wherein the device is adapted to wrap around, support and reinforce the stomach, which includes muscles and a body of a stomach, and is designed to prevent overexpansion of the stomach so that the stomach can again return back to the normal state, once the bodily material flows therethrough and into small intestines, and thereby prevent overexpansion of the stomach and limit a volume of the bodily material which can be accommodated, at any given time, by the stomach.

12. The device for wrapping around the stomach and preventing overexpansion thereof according to claim 11, wherein the device has an axial length that is longer than an axial length of the stomach so that the device partially overlaps and at least partially closes axial ends of the device so as to minimize axial expansion of the stomach when the stomach accommodates the bodily material.

13. The device for wrapping around the stomach and preventing overexpansion thereof according to claim 11, wherein the inner surface of the device is adapted to expand such that, as the bodily material flows into the stomach, the stomach increases in diameter and forces the inner surface of the device radially outwardly and thereby compressing the pliant material, located between the inner surface and the outer surface of the device, and compression of the pliant material provides resistance to further expansion of the stomach, while still permitting the bodily material to flow into and be accommodated within the stomach, and, once the bodily material passes into and through the stomach into the small intestines, the compressed pliant material and the inner surface of the device assists with forcing the stomach back into the normal state.

14. The device for wrapping around the stomach and preventing overexpansion thereof according to claim 11, wherein the device has an axial length, from the first end surface to the second end surface between 25 cm and 31 cm, the passage, in an uncompressed state, has an internal passage diameter of between 12 and 17 cm to facilitate the flow of the bodily material through the device, the outer surface of the device has an outer diameter which is in a range of between 19 cm and 30 cm, and the compressible pliant material has a thickness, in an uncompressed state of the device, which is in a range of between 4.5 cm and 12 cm.

15. A method of wrapping a device around a stomach and preventing overexpansion thereof in a radial direction as well as limiting axial lengthening thereof in an axial direction, the method comprising:
  providing a body comprising an inner surface and an outer surface, and locating a compressible pliant material between the inner surface and the outer surface of the body;
  defining a passage, that is adapted to accommodate the stomach of a patient, via the inner surface of the body, with the passage extending through the device from an inlet to an outlet of the device and the device having opposed first and second end surfaces;
  surgically implanting the device so that, following surgery, the stomach extends through the passage of the device, from the inlet to the outlet, and being completely circumferentially wrapped and surrounded by the device both in the radial direction as well as in the axial direction, between the opposed first and second end surfaces, such that an esophagus of the patient passes through the inlet of the device while a small intestine of the patient passes through the outlet of the device;
  defining, via the inner surface of the device when in an uncompressed/slightly compressed state of the device, a normal state which is configured to provide circumferential support to an exterior wall of the stomach and prevent overexpansion thereof an both the radial and axial directions while continuously permitting flow of bodily material into and through the stomach;
  providing resistance to the stomach, as the stomach attempts to expand radially from the normal state due to the bodily material flowing into and through the stomach, wherein the stomach abuts against the inner surface of the device and radially biases the inner surface of the device radially outwardly into the compressible pliant material and compresses the compressible pliant material toward the outer surface of the device and said stomach compresses the inner surface and the compressible pliant material as the exterior wall of the stomach attempts to expand, wherein said device correspondingly exerts a collapsing or resisting force against the exterior wall of the stomach, which limits and opposes expansion of the stomach and forces the exterior wall of the stomach back toward and into the normal state of the device which permits the flow of the bodily material into and through the stomach; and
  providing resistance to the stomach, as the stomach attempts to expand axially from the normal state due to the bodily material flowing into and through the stomach, wherein the stomach abuts against the inner surface of the device and axially biases the inner surface of the device axially outwardly into the compressible pliant material and compresses the compressible pliant material toward the outer surface of the opposed first and second end surfaces of the device and said stomach compresses the inner surface and the compressible pliant material as the exterior wall of the stomach attempts to expand, wherein said device correspondingly exerts a resisting and collapsing force, against the exterior wall of the stomach, which limits and opposes expansion of the stomach and forces the exterior wall of the stomach back toward and into the normal state of the device which permits the flow of the bodily material through the stomach.

* * * * *